(12) United States Patent
Field et al.

(10) Patent No.: US 7,118,870 B2
(45) Date of Patent: Oct. 10, 2006

(54) DETECTION OF FECAL CONTAMINATION USING NUCLEIC ACID MOLECULES THAT RECOGNIZE BACTERIAL 16S RDNA SEQUENCES

(75) Inventors: Katharine G. Field, Corvallis, OR (US); Anne E. Bernhard, Shoreline, WA (US)

(73) Assignee: The State of Oregon Acting by and through the State Board of Higher Education on behalf of Oregon State University, Corvallis, OR (US)

( * ) Notice: Subject to any disclaimer, the term of this patent is extended or adjusted under 35 U.S.C. 154(b) by 391 days.

(21) Appl. No.: 10/381,904

(22) PCT Filed: Sep. 28, 2001

(86) PCT No.: PCT/US01/30399

§ 371 (c)(1),
(2), (4) Date: Jul. 21, 2003

(87) PCT Pub. No.: WO02/27014

PCT Pub. Date: Apr. 4, 2002

(65) Prior Publication Data

US 2004/0033547 A1    Feb. 19, 2004

(51) Int. Cl.
*C12Q 1/68* (2006.01)
*C12P 19/34* (2006.01)
*C07H 21/04* (2006.01)

(52) U.S. Cl. .................... 435/6; 435/91.1; 435/91.2; 536/24.32; 536/24.33

(58) Field of Classification Search ................ 435/6, 435/91.1, 91.2; 536/24.32, 24.33
See application file for complete search history.

(56) References Cited

U.S. PATENT DOCUMENTS

| | | | |
|---|---|---|---|
| 5,695,946 A | 12/1997 | Benjamin et al. |
| 5,705,332 A | 1/1998 | Roll |
| 5,723,597 A | 3/1998 | Kohne |
| 6,037,122 A | 3/2000 | Mabilat et al. |

FOREIGN PATENT DOCUMENTS

| WO | WO 00/09686 A1 | 2/2000 |
|---|---|---|
| WO | WO 00/29615 | 5/2000 |

OTHER PUBLICATIONS

Langendijk et al., Applied and Environmental Microbiology 61(8), 3069-3075 (1995).*
Kreader, "Design and Evaluation of *Bacteroides* DNA Probes for the Specific Detection of Human Fecal Pollution," *Appl. Environ. Microbiol.* 61:1171-1179 (1995).
Zoetendal et al., "Temperature Gradient Gel Electrophoresis Analysis of 16S rRNA from Human Fecal Samples Reveals Stable and Host-Specific Communities of Active Bacteria," *Appl. Environ. Microbiol.* 64:3854-3859 (1998).

* cited by examiner

*Primary Examiner*—Kenneth R. Horlick
(74) *Attorney, Agent, or Firm*—Klarquist Sparkman LLP

(57) ABSTRACT

Herein disclosed are nucleic acid sequences that can be used to detect fecal contamination in a sample. In one embodiment, the probes and primers disclosed herein can be used to identify the host species that is the source of fecal bacterial contamination in the sample.

25 Claims, 8 Drawing Sheets

Fragment size (base pairs)

FIG. 2A
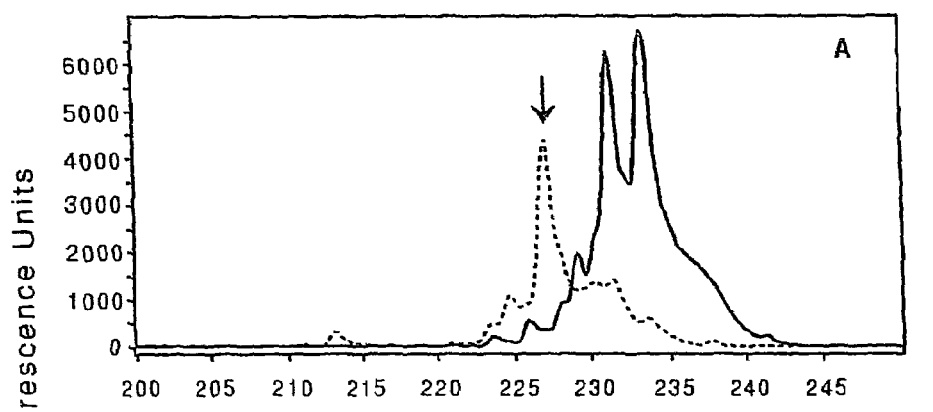
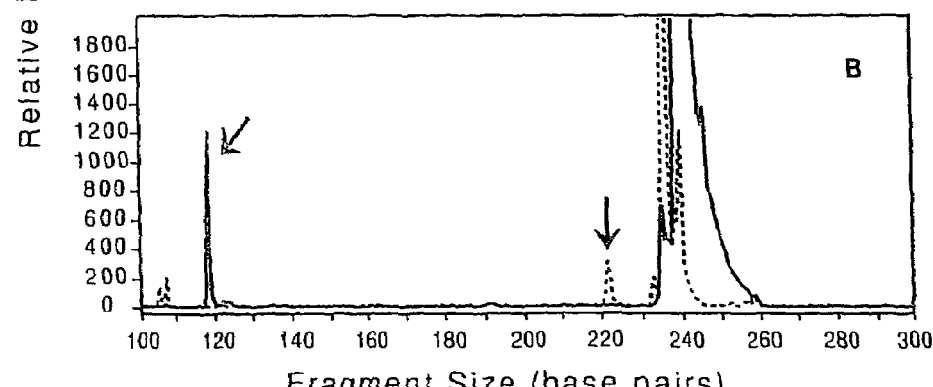
FIG. 2B

Fragment size (base pairs)

DETECTION OF FECAL CONTAMINATION USING NUCLEIC ACID MOLECULES THAT RECOGNIZE BACTERIAL 16S RDNA SEQUENCES

ACKNOWLEDGMENT OF GOVERNMENT SUPPORT

This invention was made with government support under grant No. NA76RG0476 (Project No. R/ECO-04) from the National Oceanic and Atmospheric Administration to Oregon State University under the Sea Grant College Program, with support from the U.S. Environmental Protection Agency (Grant No. R827639-01-0), and with support from the USDA (Grant No. 00-51130-9818). The government has certain rights in this invention.

CROSS-REFERENCE TO RELATED APPLICATIONS

This is the National Stage of International Application No. PCT/US01/30399, filed Sep. 28, 2001, which in turn claims the benefit of U.S. Provisional Application No. 60/236,605, filed Sep. 29, 2000.

FIELD

The present disclosures relates to nucleic acid sequences that can be used to identify the host-source of bacteria found in fecal waste.

BACKGROUND

Fecal pollution is a persistent problem, affecting many coastal and inland waters in the United States. Despite improvements in wastewater treatment technology and management practices, fecal contamination from many sources finds its way into our waters, jeopardizing the health of the ecosystems and everything that depends on them. The problem continues partly because current methods are unable to identify the source. Fecal contamination may be introduced into natural waters from a variety of sources, including ineffective sewage treatment, leaking septic systems, illegal dumping, recreational boaters, agricultural runoff, and wildlife.

Point sources, such as sewage treatment plants, can be monitored easily, and appropriate actions can be taken to reduce or eliminate the discharge. Conversely, non-point sources, such as runoff from urban and rural areas, are much more difficult to trace, and often constitute a significant portion of the contamination. Prior to the 1970's, pollution from agriculture and wildlife was considered "natural and uncontrollable" (Martin, *J. Environ. Qual.* 26:1198–203, 1997). However, several high-profile incidents involving fish kills and shellfish bed closures increased public awareness, and in 1971, the United States Army Corps of Engineers began issuing permits for discharging wastes into navigable streams and their tributaries (Id.). Since then, numerous studies have investigated the effects of agricultural runoff on bacterial pollution in natural waters (Patni et al., *Transactions of the American Society of Agricultural Engineers* 28:1871–84, 1985; Fernandez-Alvarez et al., *J. Appl. Bact.* 70:437–42, 1991; Niemi et al., *J. Environ. Qual.* 20:620–7, 1991; Miner et al., "Fecal Coliform Concentrations Measured at Various Location in the Tillamook Watershed 1965–1993", *Post Project Analysis of the Tillamook Rural Clean Water Project, Preliminary Report No. 1,* Bioresource Engineering Department, Oregon State University, Corvallis, Oreg., 1994; Edwards et al., *J. Amer. Water Resources Assoc.* 33:413–22, 1997; Stoddard et al., *J. Environ. Qual.* 27:1516–23, 1998; and Baudart et al., *J. Environ. Qual.* 29:241–250, 2000). Runoff from agricultural land is now considered one of the major sources of non-point pollution.

One of the more obvious ways that fecal pollution interferes with human activities is the introduction of pathogens commonly found in feces. Bacterial and other pathogens include organisms such as *Salmonella, Shigella, E. coli* O157:H7, *Cryptosporidium,* and *Giardia.* Viruses such as Hepatitis, Norwalk, and other enteroviruses also are often associated with feces and are detected commonly in environmental water samples (Havelaar et al., *Appl. Environ. Microbiol.* 59:2956–62, 1993; Paul et al., *Appl. Environ. Microbiol.* 63:133–8, 1997; Griffin et al., *Appl. Environ. Microbiol.* 65:4118–25, 1999; and Vantarakis et al., *Water, Air, and Soil Pollution* 114:85–93, 1999). Many of these pathogens survive in the environment (Rhodes et al., *Appl. Environ. Microbiol.* 45:1870–1876, 1983; Sinton et al., *Appl. Environ. Microbiol.* 60:2040–8, 1994; Mezrioui et al., *Water Res.* 29:459–465, 1995; Bosch et al., *Water Science and Technology* 35:243–7, 1997; Murrin et al., *Water Science and Technology* 35:429–32, 1997; Pallin et al., *J. Virol. Meth.* 67:57–67, 1997; Sinton et al., *Appl. Environ. Microbiol.* 65:3605–13, 1999), and thus are cause for concern.

In addition to pathogens carried in feces, large amounts of nutrient-rich material are introduced into receiving waters. This sudden surge of nutrients, such as nitrogen, phosphorus, and organic carbon, can cause severe imbalances in the ecosystem. For example, Cloern and Oremland (*Estuaries* 6:399–406, 1983) found increases in decomposition and nitrification, leading to anoxia, following the discharge of a large volume of primary-treated sewage into San Francisco Bay. Other studies have focused on the effects of nutrient enrichment from agricultural runoff. Phosphorus found in runoff from agricultural land was shown to increase as the proportion of land used in agricultural practices, such as dairy waste application, increased (McFarland et al., *J. Environ. Qual.* 28:836–844, 1999). This is significant because of the potential for eutrophication in phosphorus-limited freshwaters (Daniel et al., *J. Environ. Qual.* 27:251–7, 1998). Additionally, allochthonous material from non-point sources can induce algal blooms, some of which may be harmful (see Paerl, *Limnology & Oceanography* 33:823–47, 1988 for review).

Because of these imminent threats, fecal pollution is frequently monitored in many coastal waters, especially those areas used for shellfisheries and recreation. The most commonly used measure of fecal pollution are the number of viable coliforms, fecal coliforms, or *Escherichia coli* in a water sample (American Public Health Association, *Standard Methods for the Examination of Water and Wastewater,* 18th edition, Washington, D.C., American Public Health Association, 1992). Fecal coliforms are defined as gram negative, non-sporulating, rod-shaped bacteria that ferment lactose with gas formation within 24 hours at 44.5° C. (Id). They have been used as indicator bacteria for many years and are currently the Environmental Protection Agency standard for assessing water quality.

Despite the wide use of fecal coliform tests, many researchers and water resource managers have begun to question the validity of these measurements (see Toranzos et al., *Environ. Toxicol. Water Qual.* 6:121–30, 1991 for review). Although these bacteria typically originate from fecal material, fecal coliforms can survive and grow outside of enteric habitats (Flint, *J. Appl. Bact.* 63:261–70, 1987; Alkan et al., *Water Res.* 29:2071–81, 1995; Davies et al., *Appl. Environ. Microbiol.* 61:1888–96, 1995; Mezrioui et al., *Water Res.* 29:459–65, 1995; Bogosian et al., *Appl. Environ. Micro.* 62:4114–20, 1996; and Stoddard et al., *J. Environ. Qual.* 27:1516–23, 1998). They often settle in sediments, where they can grow, and then be resuspended during mixing events (Sherer et al., *Transactions of the American Society of Agricultural Engineers* 31:1217–22, 1988; Sherer et al., *J. Environ. Qual.* 21:591–5, 1992; and Davies et al., *Appl. Environ. Microbiol.* 61:1888–96, 1995). Thus, measurements of fecal coliforms may not accurately reflect recent contamination.

Ribosomal RNA is a direct gene product and is coded for by the rRNA gene. The DNA sequence for rRNA is used as a template to synthesize rRNA molecules. A separate gene exists for each of the ribosomal RNA subunits. Multiple rRNA genes exist in most organisms, higher organisms containing both nuclear and mitochondrial rRNA genes. Plants and certain other forms contain nuclear, mitochondrial, and chloroplast rRNA genes.

Numerous ribosomes are present in all cells of all life forms. About 85–90 percent of the total RNA in a typical cell is rRNA. A bacterium such as *E. coli* contains about $10^4$ ribosomes per cell while a mammalian liver cell contains about $5 \times 10^6$ ribosomes. Since each ribosome contains one of each rRNA subunit, the bacterial cell and mammalian cell contains $10^4$ and $5 \times 10^6$, respectively, of each rRNA subunit.

Nucleic acid hybridization, a procedure well known in the art, has been used to specifically detect extremely small or large quantities of a particular nucleic acid sequence, even in the presence of a very large excess of non-related sequences. Prior uses of nucleic acid hybridization are found, for example, in publications involving molecular genetics of cells and viruses, genetic expression of cells and viruses, genetic analysis of life forms, evolution and taxonomy of organisms and nucleic acid sequences, molecular mechanisms of disease processes, and diagnostic methods for specific purposes, including the detection of viruses and bacteria in cells and organisms.

Polymerase chain reaction, or PCR, produces many copies of a particular template DNA sequence in vitro. This process, well known in the art, uses nucleic acid hybridization to hybridize two primers, consisting of short DNA oligonucleotide molecules, to complementary sites on either side of the DNA sequence to be copied, or amplified. The use of a thermally-stable DNA polymerase allows repeated cycles of template denaturation, primer annealing, and synthesis of the template sequence. Specificity of the reaction is controlled by the primer design and the reaction conditions. Prior uses of PCR are found, for example, in publications involving studies of genetics of cells and viruses, genetic expression within cells, evolution and systematics of organisms, and diagnostic applications in clinical, industrial, and other settings.

SUMMARY

The present disclosure provides probes and primers which can be used to detect fecal contamination. In some embodiments, the probes and primers described herein can be used to identify the host-source of fecal bacteria. The term "host-source" refers to the organism in which the bacterium grows. For example, the host-source of a bacterium isolated from a human is human, and the host-source of a bacterium isolated from a cow is cow. In another embodiment, the probes and primers disclosed herein can be used to track any species of interest, such as environmentally important species, genetically engineered species released in the environment, and pathogens in clinical specimens. In yet another embodiment, the disclosure provides a method of detecting fecal contamination, and also its source, from environmental samples by using primers and probes targeting fecal *Bifidobacterium* and bacteria in the *Bacteroides-Prevotella* group of fecal anaerobic bacteria.

The disclosure also provides methods of using the disclosed probes and primers. These methods include contacting at least one probe or primer with a sample and detecting the binding of the probe or primer to a nucleic acid sequence in the sample, wherein the presence of binding is indicative of the presence of fecal contamination in the sample. In some embodiments, these methods use amplification reactions, such as polymerase chain reaction (PCR).

Samples can be obtained from a variety of sources. In one embodiment, a sample is a biological sample, such as a fecal or stool sample. In another embodiment, the sample is an environmental sample, such as soil, water, sediments, suspended particles, and air.

The compositions provided herein include the nucleic acid sequences shown in SEQ ID NO: 1, 3, 5, 6, 7, 8, 9, 10, 11, 12, 13, and/or 14, variants of these sequences, and stabilized forms (such as extended forms) of these sequences. In one embodiment, variant sequences are used which have 70%, 75%, 80%, 85% 90%, 92%, 95%, 98% or 99% sequence identity, which retain the ability to be used to detect fecal contamination, and in some embodiments, to identify the host-source of fecal contamination. The disclosure also provides extended forms of the nucleic acid sequences shown in SEQ ID NOS: 1, 3, and 5–14. In one embodiment, extended forms contain additional sequences that are complementary to the target nucleic acid sequence, or contain additional residues that are non-complementary to the target sequence. For example, in one embodiment, extended probes and primers contain less than about 5, 10, 15, 20, 25, 30, 50, 75, 100, 150, or 200 additional nucleic acid residues. The extended forms of the probes and primers continue to maintain the ability to detect bacteria.

Similarly, the disclosure provides fragments of the probes and primers shown in SEQ ID NOS: 1, 3, and 5–14, as well as variants of these fragments which maintain the ability to be used to detect fecal contamination, and in some embodiments, to be used to detect and/or identify the host-source of fecal contamination. For example, these fragments can be from about 5 to 19 nucleic acid residues long.

In one embodiment, the sequences disclosed herein, including variants, stabilized forms, extended forms, and fragments of SEQ ID NOS: 1, 3, and 5–14 have a detectable label. The detectable label does not interfere with the detection of fecal contamination.

Another embodiment of the disclosure provides kits having one or more of the probes and/or primers disclosed herein, for example at least two of the probes and/or primers disclosed herein. Such kits are suitable for use in detecting fecal contamination in a sample, and in some embodiments, are suitable for identification of the host-source of bacteria present in the sample. In one embodiment, the kit can be used for hybridization of the disclosed probes or primers with the sample; and/or for PCR amplification of nucleic acid sequences present in the sample using the probes and primers herein disclosed. In another embodiment, the kit comprises two or more containers, each containing at least one of the probes and/or primers disclosed herein. In a particular embodiment, a kit contains multiple, such as two or more, probes and/or primers disclosed herein which are specific for a particular environment. For example, kits can designed which contain probes and/or primers specific for the host-sources expected in a particular region, such as a particular environment Such host-sources are likely candidates as the source of fecal contamination. Instructions for use of the kit can also be included.

In yet another embodiment, the disclosed probes and primers can be used in a device that allows for DNA isolation and amplification to detect fecal contamination or its source.

These and other aspects of the disclosure will become readily apparent upon review of the following detailed description.

BRIEF DESCRIPTION OF THE FIGURES

FIGS. 2A and 2B show the results from T-RFLP analysis of 16S rDNA gene fragments amplified with Bac32F-FAM (SEQ ID NO: 1) and Bac708R (SEQ ID NO: 3) and cut with AciI (FIG. 2A) or HaeIII (FIG. 2B). Solid lines represent community profiles from human fecal DNA, and dotted lines represent community profiles from cow fecal DNA. Arrows indicate host-specific genetic markers.

FIGS. 5A and 5B show cow-specific markers 227 and 222, respectively. FIG. 5C shows the 119-bp human-specific marker.

SEQUENCE LISTING

Figure 1A:
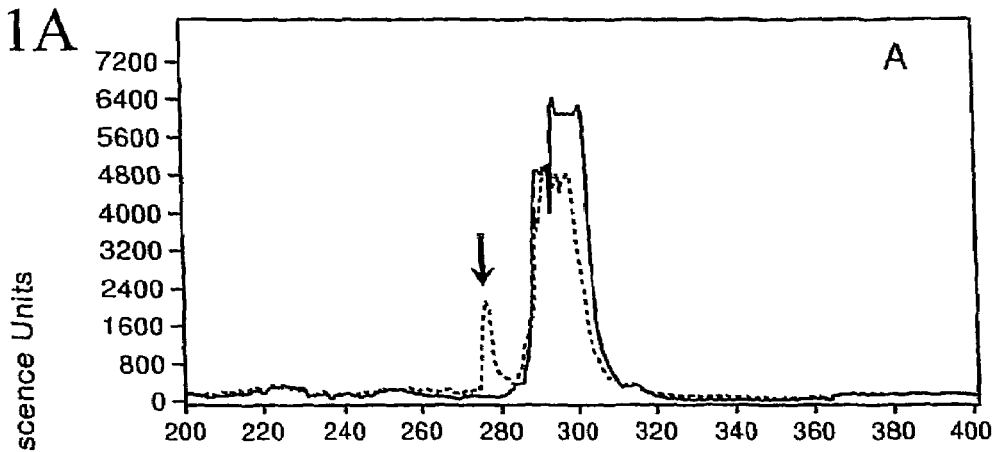
FIGS. 1A and 1B show the results from LH-PCR analysis of 16S rDNA gene fragments amplified with Bac32F-FAM (SEQ ID NO: 1) and Bac303R (SEQ ID NO: 2) (FIG. 1A) and Bif164F (SEQ ID NO: 4) and Bif601R-FAM (SEQ ID NO: 5) (FIG. 1B). Solid lines represent community profiles from human fecal DNA, and dotted lines represent community profiles from cow fecal DNA. Samples are mixtures of DNA from 7–8 individuals. The arrows indicate cow-specific gene fragments.

The nucleic acid sequences listed in the accompanying sequence listing are shown using standard letter abbreviations for nucleotide bases. Only one strand of each nucleic acid sequence is shown, but the complementary strand is understood to be included by any reference to the displayed strand.

SEQ ID NO: 1 shows the sequence of the Bac32F primer.
SEQ ID NO: 2 shows the sequence of the Bac303R primer.
SEQ ID NO: 3 shows the sequence of the Bac708R primer.
SEQ ID NO: 4 shows the sequence of the Bif164F primer.
SEQ ID NO: 5 shows the sequence of the Bif601R primer.
SEQ ID NO: 6 shows the sequence of the CF128F primer.
SEQ ID NO: 7 shows the sequence of the CF193F primer.
SEQ ID NO: 8 shows the sequence of the HF183F primer.

SEQ ID NO: 9 shows the sequence of the Elk 149F primer.

SEQ ID NO: 10 shows the sequence of the Dog 132F primer.

SEQ ID NO: 11 shows the sequence of the Cat 131F primer.

SEQ ID NO: 12 shows the sequence of the Pig 134F primer.

SEQ ID NO: 13 shows the sequence of the Pig 150F primer.

SEQ ID NO: 14 shows the sequence of the human HF134F primer.

DETAILED DESCRIPTION

Abbreviations and Terms

The following explanations of terms and methods are provided to better describe the present disclosure and to guide those of ordinary skill in the art in the practice of the present disclosure. As used herein and in the appended claims, the singular forms "a" or "an" or "the" include plural references unless the context clearly dictates otherwise. For example, reference to "a label" includes a plurality of such label and reference to "the probe" includes reference to one or more probes and equivalents thereof known to those skilled in the art, and so forth.

Unless explained otherwise, all technical and scientific terms used herein have the same meaning as commonly understood to one of ordinary skill in the art to which this disclosure belongs.

Detectable Label: A molecule capable of detection. In one embodiment, the label is conjugated to a nucleotide sequence. For example the label can be directly conjugated to a nucleic acid sequence (or to a particular nucleoside triphosphate thereof) or can become bound thereto by being bound to a specific binding agent that is attached to a probe or primer nucleotide sequence.

In general, any label that is detectable can be used. Examples of labels that can be used to practice the methods disclosed herein include, but are not limited to: isotopic or non-isotopic, catalysts such as an enzyme or a catalytic polynucleotide, promoter, dye, fluorescent molecule, chemiluminescent molecule, coenzyme, enzyme substrate, radioactive group, small organic molecule, amplifiable polynucleotide sequence, a particle such as latex or carbon, metal sol, crystallite, liposome, cell, etc., which may or may not be further labeled with a dye, catalyst, or other detectable group, and the like. In another embodiment labels include an oligonucleotide or specific polynucleotide sequence that can be added to a probe or primer to provide a template for amplification or ligation.

In one embodiment, a detectable label is a member of a signal-producing system which generates a detectable signal alone or together with other members of the signal-producing system.

DNA: Deoxyribonucleic acid. DNA is a long chain polymer which comprises the genetic material of most living organisms (some viruses have genes comprising ribonucleic acid, RNA). The repeating units in DNA polymers are four different nucleotides, each of which comprises one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

DNA construct: Refers to any nucleic acid molecule of cDNA, genomic DNA, synthetic DNA, or RNA origin. A construct is a nucleic acid segment that may be single- or double-stranded. It is understood that such nucleotide sequences include intentionally manipulated nucleotide sequences, e.g., subjected to site-directed mutagenesis, and sequences that are degenerate as a result of the genetic code.

Gene and Genome: The terms "gene" and "genome" include dsDNA (double-stranded DNA), ssDNA (single-stranded DNA), and RNA. Generally, a gene is a sequence of DNA or RNA that codes for a protein.

Isolated: An "isolated" biological component (such as a nucleic acid or protein or organelle) is a component that has been substantially separated or purified away from other biological components in the cell of the organism in which the component naturally occurs, i.e., other chromosomal and extra-chromosomal DNA, RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids.

Nucleotide: Includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligomers: Includes both oligonucleotides and analogs.

Oligonucleotide: A linear polynucleotide sequence of up to about 200 nucleotide bases in length, for example a polynucleotide (such as DNA or RNA) which is at least about 6 nucleotides, for example at least 15, 50, 100 or 200 nucleotides long.

Polynucleotide: A nucleic acid sequence (such as a linear sequence) of any length. Includes oligonucleotides and also gene sequences found in chromosomes.

Probes and primers: Nucleic acid probes and primers may be prepared readily based on the amino acid and nucleic acid sequences provided herein. Probes and primers detect their target by hybridization to complementary sequences. A "probe" comprises an isolated nucleic acid attached to a detectable label or reporter molecule. Examples of labels include, but are not limited to those listed above. Methods for labeling and guidance in the choice of labels appropriate for various purposes are discussed in, e.g., Sambrook et al. (eds.), *Molecular Cloning: A Laboratory Manual* 2nd ed., vols. 1–3, Cold Spring Harbor Laboratory Press, Cold Spring Harbor, N.Y., 1989; and Ausubel et al. (eds.) *Current Protocols in Molecular Biology*, Greene Publishing and Wiley-Interscience, New York (with periodic updates), 1987.

Primers are short nucleic acids, such as DNA oligonucleotides at least 10 nucleotides in length. A primer can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR), or other nucleic-acid amplification methods known in the art. A primer can be labeled with a detectable label and used as a probe. Primer and probe oligonucleotide sequences may be interchangeable.

Methods for preparing and using probes and primers are described, for example, in references such as Sambrook et al. (eds.), *Molecular Cloning: A Laboratory Manual*, 2nd ed., vols. 1–3, Cold Spring Harbor Laboratory Press, Cold Spring Harbor, N.Y., 1989; Ausubel et al. (eds.), *Current Protocols in Molecular Biology*, Greene Publishing and Wiley-Interscience, New York (with periodic updates), 1987; and Innis et al., *PCR Protocols: A Guide to Methods and Applications*, Academic Press: San Diego, 1990. PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with the length of the probe or primer. For example, a primer comprising 20 consecutive nucleotides will anneal to a target having a higher specificity than a corresponding primer of only 15 nucleotides. Thus, in order to obtain greater specificity, probes and primers may be selected that comprise, for example, 10, 20, 25, 30, 35, 40, 50 or more consecutive nucleotides.

Purified: Does not require absolute purity; rather, it is intended as a relative term. Thus, for example, a purified enzyme or nucleic acid preparation is one in which the subject protein or nucleotide, respectively, is at a higher concentration than the protein or nucleotide would be in its natural environment within an organism. For example, a preparation of an nucleic acid can be considered as purified if the nucleic acid content in the preparation represents at least 50%, for example at least 70%, of the total content of the preparation.

Methods for purification of proteins and nucleic acids are well known in the art. (for example see Sambrook et al. *Molecular Cloning: A Laboratory Manual*, Cold Spring Harbor, N.Y., 1989, Ch. 17).

Sample: A material to be analyzed. In one embodiment, a sample is a biological sample, such as a fecal sample. In another embodiment, a sample is an environmental sample, such as soil, sediment water, or air. Environmental samples can be obtained from an industrial source, such as a farm, waste stream, or water source.

Sequence identity: The identity/similarity between two or more nucleic acid sequences, or two or more amino acid sequences, is expressed in terms of the identity or similarity between the sequences. Sequence identity can be measured in terms of percentage identity, the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237–44, 1988; Higgins & Sharp, *CABIOS* 5:151–3, 1989; Corpet et al., *Nuc. Acids Res.* 16:10881–90, 1988; Huang et al. *Computer Appls. in the Biosciences* 8, 155–65, 1992; and Pearson et al., *Meth. Mol. Bio.* 24:307–31, 1994. Altschul et al., *J. Mol. Biol.* 215:403–10, 1990, presents a detailed consideration of sequence alignment methods and homology calculations.

The NCBI Basic Local Alignment Search Tool (BLAST) (Altschul et al, *J. Mol. Biol.* 215:403–10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

One indication that two nucleic acid molecules are closely related is that the two molecules hybridize to each other under stringent conditions. Stringent conditions are sequence-dependent and are different under different environmental parameters.

Subject: Includes any organism, for example a mammalian subject, such as a human or veterinary subject.

Substantial similarity: A first nucleic acid is substantially similar to a second nucleic acid if, when optimally aligned (with appropriate nucleotide deletions or gap insertions) with the other nucleic acid (or its complementary strand), there is nucleotide sequence identity in at least about, for example, 50%, 75%, 80%, 85%, 90%, 92%, 95%, 98%, or 99% of the nucleotide bases. One of skill in the art will appreciate that these ranges are provided for guidance only; it is possible that substantially similar nucleic acids could be obtained that fall outside the ranges provided.

Sequence similarity can be determined by comparing the nucleotide sequences of two nucleic acids using the BLAST™ sequence analysis software (blastn) available from The National Center for Biotechnology Information. Such comparisons may be made using the software set to default settings (expect=10, filter=default, descriptions=500 pairwise, alignments=500, alignment view=standard, gap existence cost=11, per residue existence=1, per residue gap cost=0.85).

Experimental Overview

The methods disclosed herein were used to identify genetic markers from fecal bacteria from several hosts, that identify feces from these hosts. Using the sequence data for the markers, the primers disclosed herein were designed that are specific for each genetic marker. These primers can be used to identify the most likely sources of fecal contamination in samples. Using the methods disclosed herein, markers for other organisms that are likely to be a cause of pollution can be identified. For example, other sources of fecal pollution include waterfowl and deer, and other common wildlife. In addition, probes and primers can be designed based on the methods disclosed herein to detect fecal contamination that results from such wildlife.

Fecal samples were collected from human and cow sources and DNAs extracted. The 16S rDNA fragments from these samples were amplified using primers specific for *Bacteroides* or *Bifidobacterium*. Length Heterogeneity Polymerase Chain Reaction (LH-PCR) and Terminal Restriction Fragment Length Polymorphism (T-RFLP) were used to identify regions of DNA that were specific to bacteria isolated from humans and cows (host-specific DNA). Two human-specific and three cow-specific markers were identified. These markers were used to isolate and clone 16S rDNA fragments. The sequencing of these fragments allowed a phylogenetic analysis to be performed. The markers clustered into three host-specific clusters.

Samples were taken from various natural bodies of water and tested using the LH-PCR and T-RFLP techniques to determine whether the identified fecal markers could be recovered from water. The host-specific markers were recovered from the environmental samples and sequence analysis confirmed their identities.

The initially identified markers then were used to clone additional rDNA fragments from polluted water. These fragments were sequenced and found to be members of the same three phylogenetic clusters. The combined sequence data (data from the initial screen and data from the additional rDNA clones) were used to develop additional PCR primers diagnostic for fecal source.

Environmental samples were collected and analyzed using both the primers that were initially designed to identify the genetic markers and the additional primers designed from subsequent isolations. These environmental samples were collected from various sites in the state of Oregon. The samples that tested positive for rDNA derived from fecal matter were analyzed to see if they correlated with known point and non-point sources of pollution.

Fecal samples from additional animal species (dog, cat, elk, and pig) were collected and DNAs were extracted as described above. Specific primers were used to amplify *Bacteroides* rDNAs and rDNA clone libraries were constructed. The clones were sequenced and compared by phylogenetic analysis. Gene clusters or regions of bacterial gene sequences that only occurred in a particular animal host species were identified and used to design additional primers diagnostic for fecal contamination from these animal species.

These primers are useful for identifying point-source contamination, and non-point-source contamination, and to follow spatial and temporal fluctuations in specific bacterial groups in the natural environment.

EXAMPLE 1

Fecal Sample Collection

Human fecal samples were donated by healthy adult and child volunteers from Corvallis, Oreg., including Caucasian, Asian, and Hispanic individuals. Samples were collected in sterile containers and stored at −80° C. Fresh cow fecal samples were collected from healthy Holstein dairy cows from two farms in Corvallis, Oreg., and three farms in Tillamook County, Oregon. The Corvallis cow fecal samples were collected during three different seasons from 1996 to 1998, and Tillamook County cow fecal samples during Fall 1996. Wild elk feces were collected from several locales in the Oregon Coast Range. Pig feces were collected from three farms near Corvallis, Oreg. Dog and cat feces were collected from pets in Corvallis, Oreg., and from the Heart of the Valley Humane Society, Corvallis, Oreg. Samples were collected with sterile utensils and placed in sterile 50-mL tubes, kept on ice for transport to the lab, and stored at −80° C.

Environmental samples were collected from multiple bay and river sites in the Tillamook watershed and from sewage treatment facilities in Corvallis and Tillamook, Oreg. The collection sites selected represented three rivers, the Tillamook, the Trask, and the Wilson, that are frequently contaminated with fecal pollution, and four sites along a north-south transect starting near the confluence of the Tillamook and Trask rivers and ending at a site near the mouth of the estuary. Water samples were collected in sterile 1-liter containers from surface waters and stored on ice during transport. Upon return to the lab, the samples were filtered through 0.2 μm Supor-200 filters (Gelman, Ann Arbor, Mich.). Filters were placed in separate plastic bags or 50 mL disposable centrifuge tubes with 5 mL of lysis buffer (20 mM EDTA, 400 mM NaCl, 750 mM sucrose, 50 mm Tris, pH 9) and stored at −80° C. Fecal coliform concentrations were tested according to standard methods (American Public Health Association, *Standard Methods for the Examination of Water and Wastewater*, 18$^{th}$ edition, Washington, D.C., American Public Health Association, 1992).

EXAMPLE 2

DNA Extractions

DNA was extracted by bead-beating using the method of Gray and Herwig (*Appl. Environ. Microbiol.* 62:4049–59, 1996) with the following modifications: 0.5 g of 0.1-mm diameter glass beads (acid-washed and baked) were used, polyvinylpolypyrrolidone was omitted from the lysis buffer, and crude extracts were ethanol-precipitated. The resulting pellets were dried under vacuum and resuspended in InstaGene Matrix (BioRad, Hercules, Calif.) or TE (10 mM Tris, 1 mM EDTA, pH 8). The DNA extracts were purified by phenol/chloroform extractions followed by ethanol precipitation and resuspension in TE. DNAs from elk, pig, cat, and dog feces were extracted with a Qiagen DNEasy kit according to the manufacturer's directions.

DNA from the water samples was extracted based on the method of Giovannoni et al. (*Appl. Environ. Microbiol.* 56:2572–5, 1990) except the cesium trifluouroacetic acid (CsTFA) purification steps were omitted. Instead, samples were cleaned using one of the following methods: 1) one volume of 20% polyethylene glycol 8000 in 2.5 M NaCl was added, samples incubated for 15 minutes at 37° C. and centrifuged for 10 minutes at 12,500 rpm, and the resulting pellets washed twice with ice-cold 80% ethanol; 2) guanidine thiocyanate (Fluka, Buchs, Switzerland) purification based on the method of Pitcher et al. (*Letters in Applied Microbiology* 8:151–6, 1989), or 3) polyvinylpolypyrrolidone (Aldrich, Milwaukee, Wis.) spin columns (Berthelet et al., *FEMS Microbiology Letters* 138:17–22, 1996).

EXAMPLE 3

Analysis of Fecal DNA to Identify Host-Specific Markers

Approximately 2–4 ng of fecal DNAs from individual humans, cows, elks, pigs, dogs and cats, were amplified by the PCR. In addition to analyzing individual samples, pooled PCR products from multiple individuals from each host species were also analyzed. DNAs from fourteen human samples were amplified with both *Bacteroides/Prevotella* and *Bifidobacterium* primers (Table 1). DNAs from eight Corvallis and eight Tillamook cows were amplified with *Bacteroides/Prevotella* primers, but only four each with *Bifidobacterium* primers. Each 50 µL PCR contained 1×TAQ™ polymerase buffer, 10 µM each primer, 200 µM each dNTP, 1.25 units of TAQ™ polymerase, 640 ng/µL BSA (Kreader, *Appl. Environ. Microbiol.* 62:1102–6, 1996), and 1.5 mM MgCl$_2$.

TABLE 1

Primers used to identify genetic markers.

| Primer* | Primer Sequence (5'-3') | | Target |
|---|---|---|---|
| Bac32F | AACGCTAGCTACAGGCTT | (SEQ ID NO: 1) | *Bacteroides/Prevotella* |
| Bac303R | CCAATGTGGGGGACCTTC | (SEQ ID NO: 2) | *Bacteroides/Prevotella* |
| Bac708R | CAATCGGAGTTCTTCGTG | (SEQ ID NO: 3) | *Bacteroides/Prevotella* |
| Bif164F | GGGTGGTAATGCCGGATG | (SEQ ID NO: 4) | *Bifidobacterium* |
| Bif601R | TAAGCGATGGACTTTCACACC | (SEQ ID NO: 5) | *Bifidobacterium* |

*Bac = *Bacteroides/Prevotella*, Bif = *Bifidobacterium*; numbering corresponds to *E. coli* 16S rRNA gene.

Bif601R (SEQ ID NO: 5) and Bac32F (SEQ ID NO: 1) were labeled with the fluorophore 6-FAM (GenSet, La Jolla, Calif.). Non-fluorophore labeled primers Bac303R (SEQ ID NO: 2), Bac708R (SEQ ID NO: 3), and Bif164F (SEQ ID NO: 4) were synthesized by Gibco BRL (Gaithersburg, Md.). Primers (Bif601R (SEQ ID NO: 5), Bac32F (SEQ ID NO: 1), and Bac708R (SEQ ID NO: 3) were designed using the Probe Design function of ARB (Strunk et al., ARB, *A Software Environment for Sequence Data*, Munich, Technische Universitat Munchen, 1996) and confirmed using CHECK_PROBE analysis of the Ribosomal Database Project (Maidak et al., *Nucleic Acids Res.* 22:3485–7, 1994) and Probe Match of ARB. Primer specificity was established using DNA from cultured *Bacteroides* and *Bifidobacterium*. A thermal mini-cycler (MJ Research, Watertown, Mass.) was used for all reactions with the following conditions: 35 cycles of 94° C. for 30 seconds, 53° C. for 1 minute, 72° C. for 2 minutes, followed by a final six-minute extension at 72° C. The products were quantified in a 1% agarose gel by comparing the band intensity to a low molecular weight DNA mass ladder (Gibco BRL).

Restriction enzymes were chosen based on analysis of published sequences in GenBank using Mapsort (Genetics Computer Group, Wisconsin). Enzymes that produced the greatest number of terminal restriction fragments of different length within the *Bacteroides/Prevotella* or *Bifidobacterium* 16S rDNA sequences were tested empirically. Enzymes were purchased from New England Biolabs (Beverly, Mass.). PCR products amplified using Bac32F (SEQ ID NO: 1) and Bac708R (SEQ ID NO: 3) were digested overnight at 37° C. with either AciI or HaeIII. PCR products amplified using Bif164F (SEQ ID NO: 4) and Bif601R (SEQ ID NO: 5) were digested overnight with HaeIII (at 37° C.) or TaqI (at 65° C.). Each 20 µL digestion contained 20–40 ng of PCR products, 10 units of enzyme, 1× enzyme buffer, and 100 µg/ml BSA (for TaqI only).

The fragments generated were separated by size on an ABI DNA sequencer with GeneScan software, allowing for the identification of DNA fragment lengths unique to either humans or cows. From these analyses, seven potential host-specific 16S rDNA genetic markers from human and cow fecal DNAs were identified by LH-PCR or T-RFLP analysis of human and cow fecal DNAs (Table 2). To be considered a host-specific genetic marker, the gene fragment had to be present in all samples from that host and be absent from all samples from the other host.

TABLE 2

Potential host-specific genetic markers.

| Host specificity | Primer Pair | Enzyme Used | Size of marker fragment (bp)* |
|---|---|---|---|
| human | Bac32F (SEQ ID NO: 1)– Bac708R (SEQ ID NO: 3) | HaeIII | 119 |
| cow | Bac32F (SEQ ID NO: 1)– Bac708R (SEQ ID NO: 3) | HaeIII | 222 |
| cow | Bac32F (SEQ ID NO: 1)– Bac708R (SEQ ID NO: 3 | AciI | 227 |
| cow | Bac32F (SEQ ID NO: 1)– Bac303R (SEQ ID NO: 2) | none | 276 |
| cow | Bifl64F (SEQ ID NO: 4)– Bif601R (SEQ ID NO: 5) | HaeIII | 142–152 |
| human | Bifl64F (SEQ ID NO: 4)– Bif601R (SEQ ID NO: 5) | TaqI | 313 |
| cow | Bifl64F (SEQ ID NO: 4)– Bif601R (SEQ ID NO: 5) | none | 453 |

*Markers are located within the 16S rRNA genes from *Bacteroides* or *Bifidobacterium*.

LH-PCR analysis, which detects length differences in PCR amplicons, revealed *Bacteroides/Prevotella* and *Bifi*-

Figure 1B:
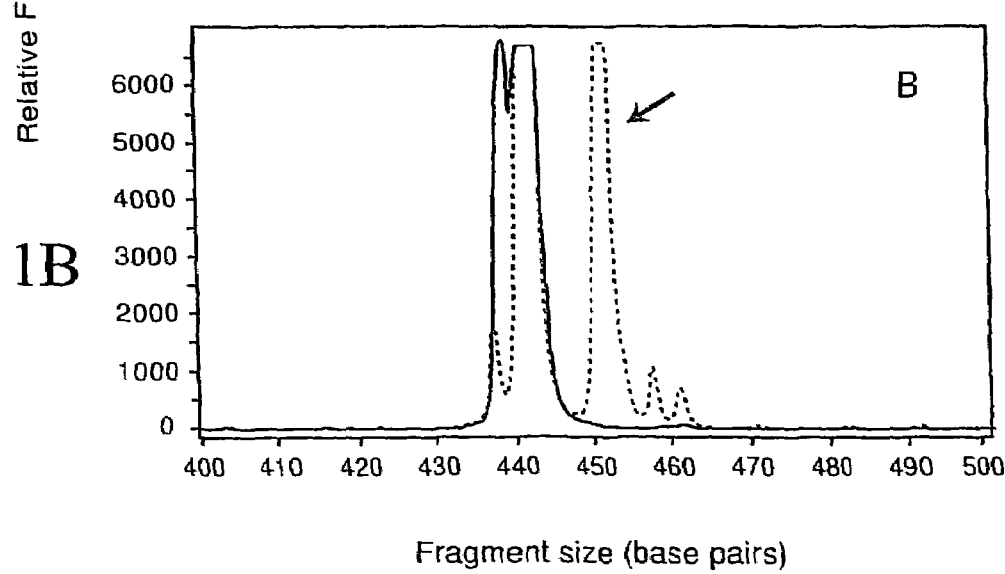

*dobacterium* cow-specific genetic markers (FIG. 1). LH-PCR analysis of 16S rDNA amplicons amplified with Bac32F (SEQ ID NO: 1) and Bac708R (SEQ ID NO: 3) from human and cow feces identified a peak at 276 bp as a potential cow-specific gene fragment, but no human-specific genetic markers were detected. LH-PCR analysis of 16S rDNA amplicons amplified with Bif164F (SEQ ID NO: 4) and Bif601R (SEQ ID NO: 5) revealed a cow-specific genetic marker at 453 bp.

Five additional host-specific genetic markers were identified by cutting *Bacteroides/Prevotella* or *Bifidobacterium* PCR amplicons with restriction endonucleases and analyzing the fluorescently-labeled terminal end fragments for size differences (T-RFLP). Host-specific peaks, corresponding to terminal end fragments, were identified in T-RFLP analyses of human and cow fecal DNAs (FIGS. 2A, 2B, 3A, and 3B). When PCR products amplified with Bac32F (SEQ ID NO: 1) and Bac708R (SEQ ID NO: 3) were digested with AciI, one cow-specific peak (arrow, dotted line) was found at 227 bp (FIG. 2A). There were additional host-specific peaks (solid line), which, upon sequence analysis, were discovered to be artifacts produced by partial digestion. Analysis of 16S rDNA amplicons from human feces and sewage amplified with Bac32F (SEQ ID NO: 1) and Bac708R (SEQ ID NO: 3) and digested with HaeIII revealed a 119-bp human-specific peak (arrow, solid line) and a cow-specific peak of 222 bp (arrow, dotted line; FIG. 2B).

Figure 3A:
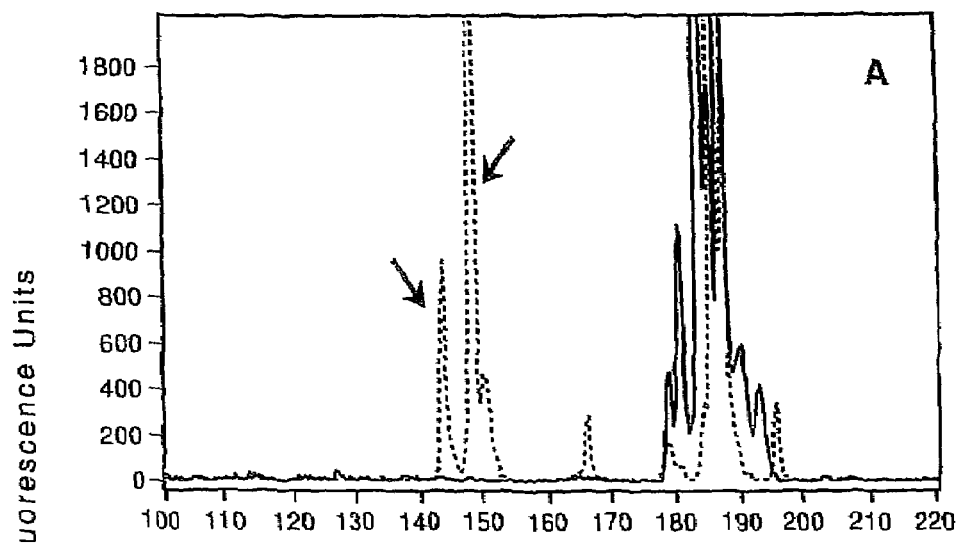
FIGS. 3A and 3B show the results from T-RFLP analysis of 16S rDNA gene fragments amplified with Bif164F (SEQ ID NO: 4) and Bif601R-FAM (SEQ ID NO: 5) and cut with HaeIII (FIG. 3A) or TaqI (FIG. 3B). Solid lines represent community profiles from human fecal DNA; dotted lines represent community profiles from cow fecal DNA. Arrows indicate host-specific genetic markers.
Figure 3B:
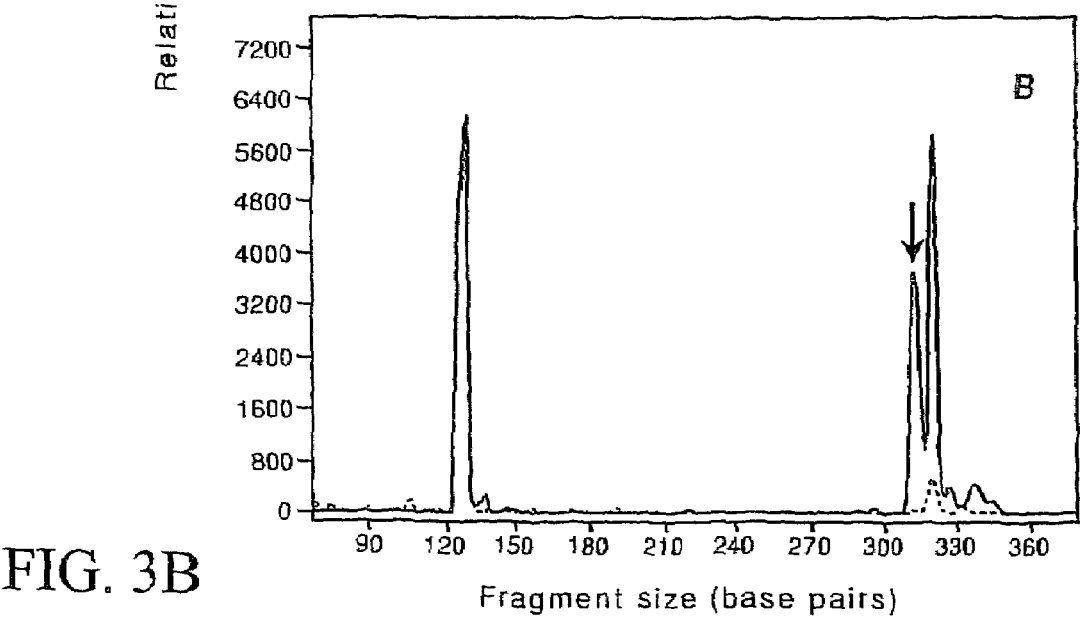

T-RFLP analysis of 16S rDNA genes amplified from cow feces using Bif164F (SEQ ID NO: 4) and Bif601R (SEQ ID NO: 5) and cut with HaeIII revealed a cow-specific cluster of peaks (arrows, dotted line) ranging from 142–152 bp (FIG. 3A). Analysis of 16S rDNA amplicons from human feces and sewage amplified with Bif164F (SEQ ID NO: 4) and Bif601R (SEQ ID NO: 5) and digested with TaqI produced a human-specific peak at 313 bp (arrow, solid line), but no cow-specific peaks were detected in the amplicons from cow feces (FIG. 3B).

Comparison of *Bacteroides/Prevotella* and *Bifidobacterium* communities in sewage samples from two Oregon cities, Corvallis and Tillamook, and feces from 14 humans revealed very similar community profiles for both *Bacteroides/Prevotella* and *Bifidobacterium*, although sometimes there were differences in proportions of LH-PCR and T-RFLP peaks present. Similarly, DNA from cow feces collected at different times of the year, from different farms and different towns, revealed similar patterns. These results demonstrate that, although there may be slight intraspecies variation at the level of variability detected by these markers, the host-specific patterns are the same.

All analyses were performed using samples from individuals as well as host-specific community samples. Approximately 25 fmols of PCR products or restriction digest products were resolved on a Long Ranger polyacrylamide gel (FMC, Rockland, Me.) on an ABI 377 automated DNA sequencer using GeneScan software (Applied Biosystems Inc., Fremont, Calif.). The internal size standard, GENESCAN2500-ROX™ (ABI) was loaded in each lane. Fragment sizes were estimated using the Local Southern Method in GeneScan™ software v.2.1 (ABI).

EXAMPLE 4

Recovery of Unique Fecal Markers from Natural Water Samples

Figure 5A:
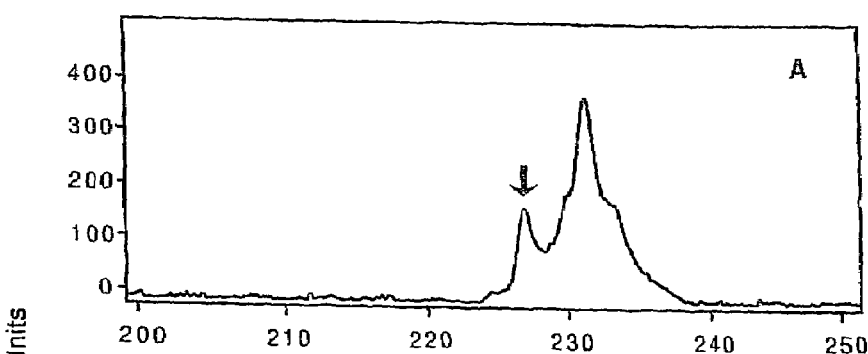
FIGS. 5A–5C show results from T-RFLP analyses of 16S rDNA gene fragments amplified from DNA extracted from Tillamook Bay water samples. DNA was amplified using Bac32F (SEQ ID NO: 1) and Bac708R (SEQ ID NO: 3) and digested with AciI (FIG. 5A) or HaeIII (FIGS. 5A and 5B). Arrows indicate host-specific markers.
Figure 5B:
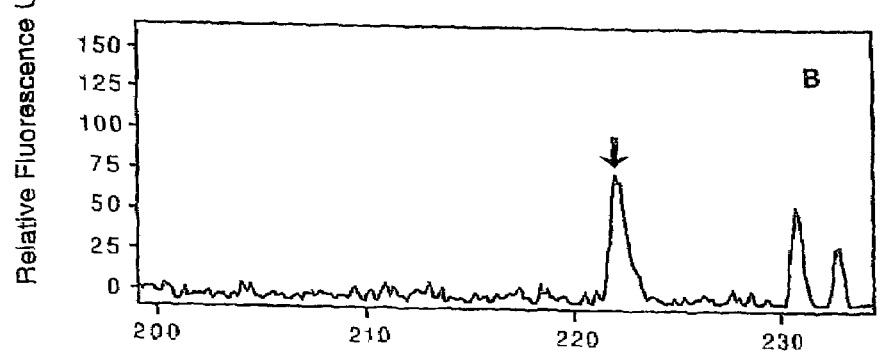
Figure 5C:
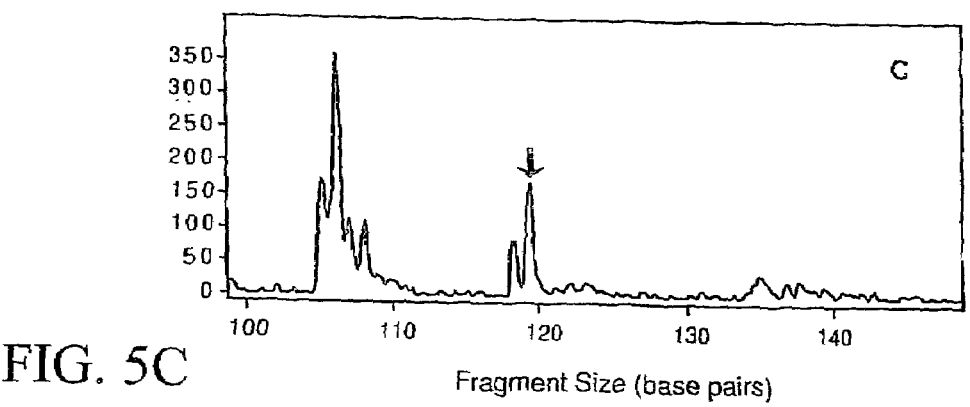
Figure 8:
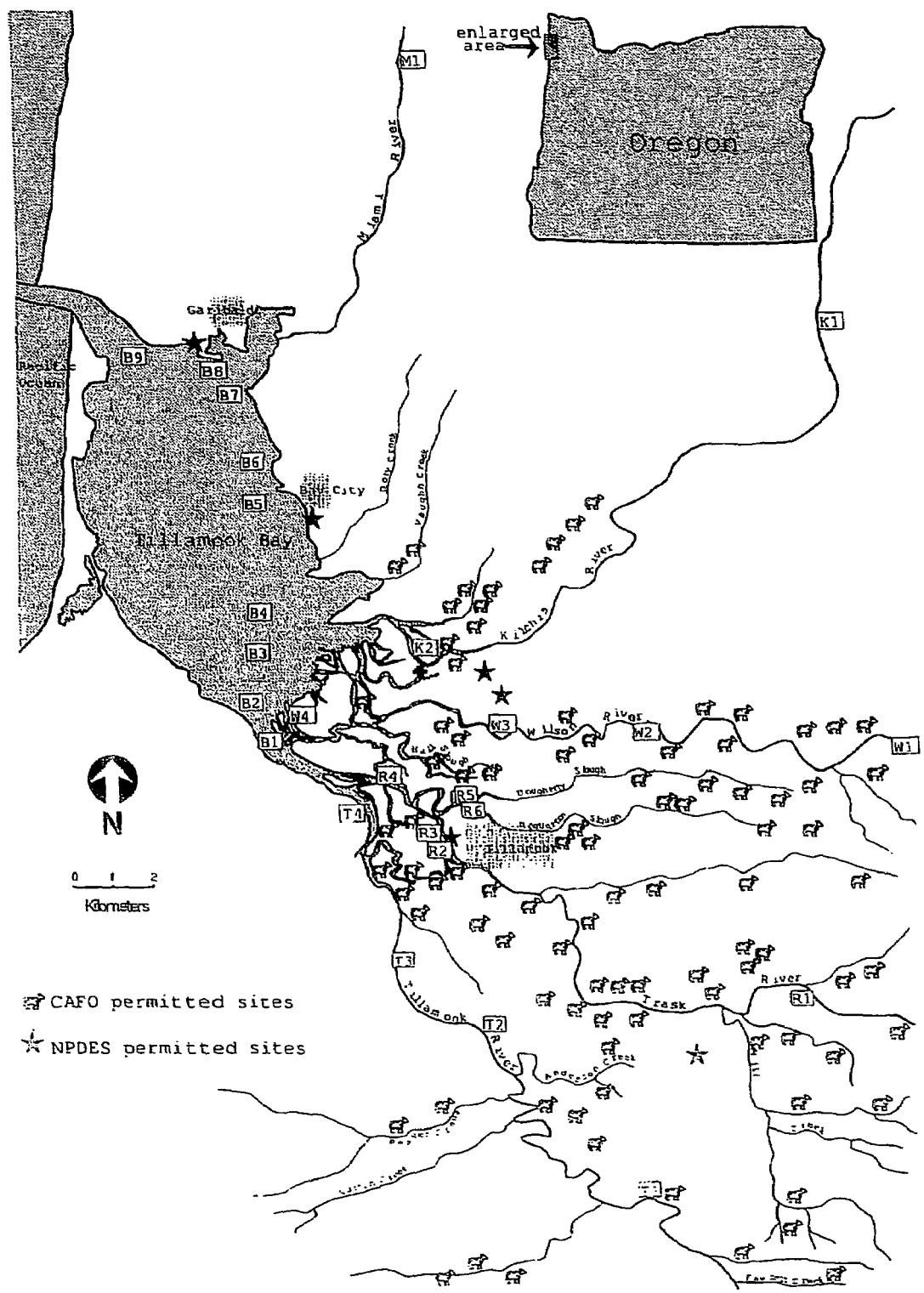
FIG. 8 shows a map of the sample testing area.

To test whether the species-specific fecal markers could be detected in natural waters, samples were collected from Tillamook Bay, Oreg., and its tributaries. Tillamook Bay is a shallow estuary on the northwest coast of Oregon (FIG. 8). It is approximately 3.2 km wide and 11.3 km long, with an estimated 3,590 hectares of surface water at high tide. Its watershed covers nearly 150,000 hectares, and is drained by five major rivers, the Miami, the Kilchis, the Tillamook, the Trask, and the Wilson Rivers. Ninety-one percent of the watershed is forested; about 8% is in farmland, with an estimated 22,000 dairy cattle (Dorsey-Kramer, *A Statistical Evaluation of the Water Quality Impacts of Best Management Practices Installed at Tillamook County Dairies*, Master's Thesis, Oregon State University, Corvallis, Oreg., p. 208, 1995). The bay is also the site of commercial and recreational fisheries, including one of Oregon's primary oyster growing areas. Additional water samples were collected, DNAs were extracted and analyzed by LH-PCR or T-RFLP as discussed above. The unique fecal markers were recovered from numerous water samples (FIGS. 5A–5C).

EXAMPLE 5

Fecal DNA Library Construction and Analysis

DNAs from individual cow, human, elk, dog, cat, or pig fecal samples, or from water samples, were amplified with Bac32F (SEQ ID NO: 1) and Bac708R (SEQ ID NO: 3), and amplicons from 10 individuals from each host species were pooled. PCR products were gel-purified using the Qiaquick Gel Extraction Kit (Qiagen, Valencia, Calif.) and cloned using the pGEM-T Easy Cloning Kit (Promega, Madison, Wis.) according to the manufacture's directions. One hundred ninety-two transformants were randomly selected from each library and inoculated into 100 ml LB broth with 100 g/ml ampicillin in 96-well microtiter plates. After a six-hour incubation, two replica plates were made from each original microtiter plate. All plates were incubated overnight at 37 C. The next day, clones from each row in a microtiter replica plate and clones from each colony in another microtiter replica plate were pooled.

DNAs from the pooled rows and columns from the human, cow, or water libraries were amplified using Bac32F (SEQ ID NO: 1) and either Bac303R (SEQ ID NO: 2) or Bac708R (SEQ ID NO: 3). Bac32F (SEQ ID NO: 1) was labeled with the fluorophore 6 FAM. PCR products amplified with Bac32F (SEQ ID NO: 1) and Bac303R (SEQ ID NO: 2) were analyzed by LH-PCR. PCR products amplified with Bac32F (SEQ ID NO: 1) and Bac708R (SEQ ID NO: 3) were digested with the restriction enzymes HAEIII or ACII as described above and analyzed by T-RFLP. The clones on each microtiter plate corresponding to each genetic marker were identified by locating the intersection of a positive result in a row with a positive result in a column.

To identify unique sequence types in elk, dog, cat and pig clone libraries, DNA from each clone was subjected to T-RFLP analysis with Hae-III as described above. Multiple representatives of each unique T-RFLP pattern were chosen for sequencing.

EXAMPLE 6

Sequencing of Marker Clones

As described above, the initial data gathered using the PCR primers provided in Table 1, were used to identify and sequence additional clones. Plasmid DNAs from overnight cultures were prepared using the Qiaprep Spin Column Purification Kit (Qiagen) according to the manufacturer's directions. DNA was quantified spectrophotometrically on a Shimadzu (Columbia, Md.) UV/Vis spectrophotometer. Bidirectional sequences were obtained using T7 and SP6 priming sites on either side of the insert. Sequences were determined on an ABI 377 DNA Sequencer using dye-terminator chemistry.

EXAMPLE 7

Phylogenetic Analysis

Sequences were subjected to analysis using BLAST v. 2.0 to obtain preliminary closest phylogenetic neighbors. The sequences were aligned manually to sequences from the *Cytophaga-Flavobacter-Bacteroides* group obtained from GenBank using the DNA sequence editor in GCG™ v.10 (Genetics Computer Group, Wisconsin). Sequences and alignments were verified by comparisons to the 16S rRNA secondary structure of *Bacteroides fragilis* and to *Bacteroides* signature sequences (Gherna et al., *System. Appl. Microbiol.* 15:513–21, 1992). Evolutionary distances were calculated using the DNADIST™ program with the Kimura 2-parameter model for nucleotide change and a transition/transversion ratio of 2.0 (Kimura, *J. Mol. Evol.* 16:111–20, 1980). Phylogenetic trees were inferred by the neighbor-joining algorithm (Saitou et al., *Mol. Biol. Evol.* 4:406–25, 1987) using the NEIGHBOR™ program in PHYLIP™ 3.5c (Felsenstein, *Cladistics* 5:164–6, 1989). Regions of ambiguous alignment were excluded from the analyses. To check the consistency of the resulting tree, the sequences were randomly resampled 100 times (bootstrapping) and a consensus tree was obtained (Felsenstein, *Evolution* 39:783–91, 1985). Similarities were calculated using Similarity Matrix™ v.1.1 from the Ribosomal Database Project.

Further analysis of these sequences revealed that the fragment size estimated by T-RFLP was 1 bp smaller than the actual size (120 bp) determined from the sequences. Four of these sequences (HF8, HF102, HF117 and HF145), although not identical, were >98.9% similar to each other and were 97.5–98.0% similar to *B. vulgatus*. These sequences formed the closely related HF8 gene cluster (FIG. 4), but did not match any published sequence exactly. HF74 was 93.9–94.9% similar to the clones in the HF8 cluster and 93.2% similar to *B. vulgatus*. One other human fecal clone, HF10, was 97.7% similar to *B. uniformis*.

Figure 4:
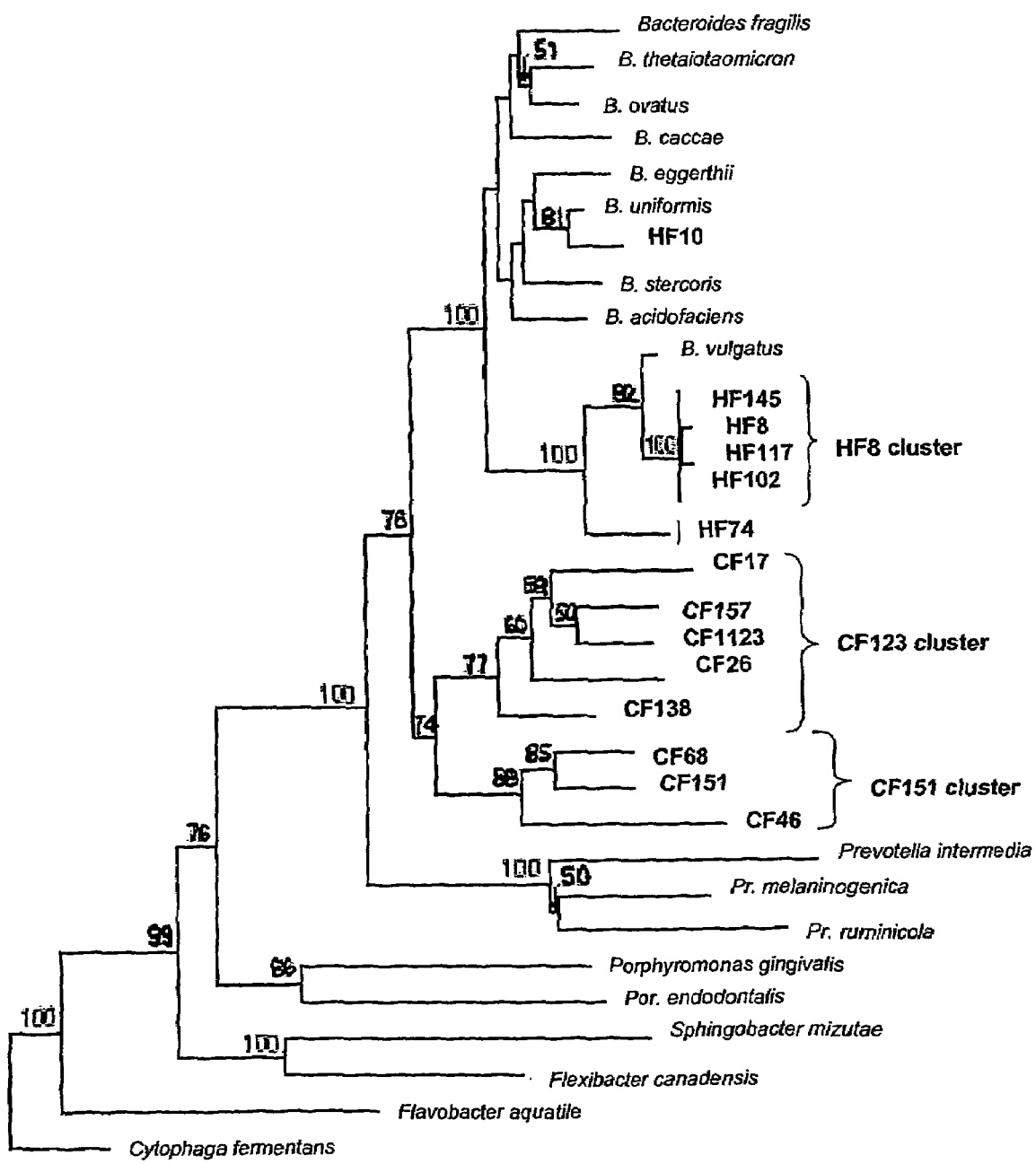
FIG. 4 shows a tree of phylogenetic relationships among partial 16S rDNA sequences (558 positions) of human (HF) and cow (CF) host-specific genetic markers identified from fecal clone libraries. The tree was inferred by neighbor-joining. Numbers above the internal branches are percentages of bootstrap replicates that support the branching order. Bootstrap values below 50% are not shown. *Cytophaga fermentans* was used to root the tree.

None of the cow-specific clones was closely related to any characterized microorganisms. These clones formed two distinct gene clusters within the *Cytophaga-Flavobacter-Bacteroides* phylum (FIG. 4). Seven clones were recovered from cow feces that produced the 227 bp size fragment, when amplified with Bac32F (SEQ ID NO: 1) and Bac708R (SEQ ID NO: 3), and cut with AciI. Partial 16S rDNA sequencing revealed five different sequences, each with the same T-RFLP profile, which formed the CF123 gene cluster. Fragment sizes estimated by T-RFLP analysis were about two bases larger than the size determined from the sequences (225 bp). Similarities ranged from 91.6–95.2% within this cluster. Sequence analysis of the clones corresponding to the 222 bp (T-RFLP with HaeIII) and the 276 bp (LH-PCR) cow-specific markers revealed that these markers represented the same sequences. Four clones were found representing three different sequences that corresponded to these two markers. These three sequences were 92–94.4% similar, and all were included in the CF151 gene cluster (FIG. 4). Again, fragment sizes estimated by T-RFLP and LH-PCR were 1–2 bases different from the sizes predicted from the sequences.

The discovery of new gene clusters within the *Bacteroides/Prevotella* group from cows reflects the lack of characterization of diversity within this habitat. Conversely, the human intestinal flora is a better characterized habitat, due to the clinical significance of these bacteria. Microbial diversity of human fecal and colonic bacteria has been the subject of many culture-based studies, but only since the application of molecular techniques have researchers had the tools to assess the diversity more accurately. Although culture bias may be less of a problem in enriched, highly selective environments such as feces, it is still likely to occur, especially for anaerobic bacteria that may be difficult to grow (Amann et al., *Microbiological Reviews* 59:143–169, 1995). Comparisons of 16S rDNA diversity with that assessed by culture methods in human feces (Wilson et al., *Appl. Environ. Microbiol.* 62:2273–8, 1996; and Wood et al., *Appl. Environ. Microbiol.* 64:3638–89, 1998) and bovine rumens (Krause et al., *J. Dairy Science* 79:1467–75, 1996) indicating an underestimation of diversity by culturing alone.

The clones comprising the HF8 cluster were >99% similar, with the exception of HF102. These three clones (HF8, HF117, HF145) varied by only 1–2 nucleotides over a 700-base sequence, which falls within predicted TAQ™ polymerase error rates (Saiki et al., *Science* 239:487–91, 1988). Three of the six deviant nucleotides were consistent with common TAQ™ errors (Dunning et al, *Nucl. Acids Res.* 16:10393, 1988; and Tindall et al., *Biochem.* 27:6008–13, 1988), and two others were incompatible with secondary structure, indicating PCR or sequencing errors. It is possible that these three sequences are actually the same. Although HF102 was in the same gene cluster, it had 9–11 nucleotide differences from the other three sequences in this cluster. However, these differences were in a hypervariable region of the gene.

Figure 6:
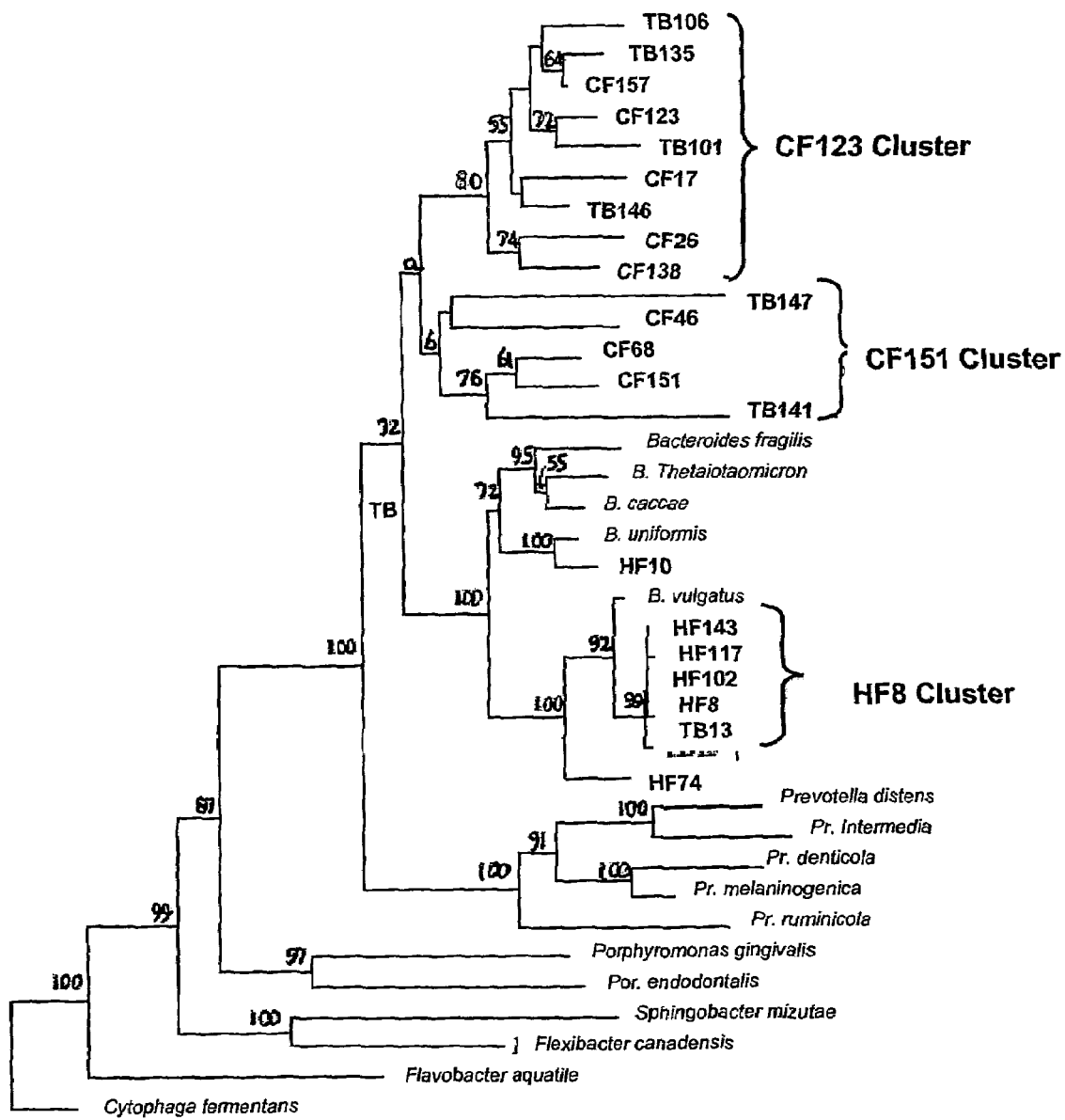
FIG. 6 shows a tree of phylogenetic relationships among partial 16S rDNA sequences (558 positions) of clones recovered from Tillamook Bay water samples (TB). HF and CF are host-specific genetic markers identified from human or cow fecal clone libraries, respectively. The tree was inferred by neighbor-joining. Numbers above the internal branches are percentages of bootstrap replicates that support the branching order. Bootstrap values below 50% are not shown. Bootstrap values for a and b dropped from 68 to 47 and 76 to 40, respectively, when TB147 was added to the analysis. *Cytophaga fermentans* was used to root the tree.

Sequence analysis of the additional clones recovered from water samples revealed seven unique clones that corresponded to the human or cow genetic markers previously identified. All of the clones were very similar, but not identical, to clones recovered from human and cow fecal samples (FIG. 6). To confirm that the clones recovered from water samples were fecal in origin, primers were designed that were specific to two of the water clones, TB141 and TB147. These primers were used to amplify 16S rRNA genes from cow fecal DNAs. Sequence analysis of the PCR products confirmed that the sequences were the same as the respective sequences of the two clones.

Six of the seven clones recovered from water samples clustered with human or cow-specific sequences identified earlier (FIG. 4). TB13 corresponded to the human-specific cluster, HF8, and was greater than 99% similar to other clones in this cluster. The TB13 sequence differed by only 1–2 bases from HF8, HF117, and HF145. The remaining clones corresponded to the cow-specific markers. TB141 had the same T-RFLP pattern as CF46, CF68, and CF151 and was 84.7% to 90.4% similar to the other CF151 clones. TB101, TB106, TB135 and TB146 had the same T-RFLP pattern as the other clones in the CF123 cluster and were 93.3 to 96.1% similar. The T-RFLP pattern of TB147 matched the patterns of the CF123 cluster, but the sequence grouped with the CF151 cluster (FIG. 6). Additionally, TB147 had the highest similarity with CF17 (88.2%), which is in the CF123 cluster. Bootstrap values for the CF151 cluster dropped considerably when TB147 was included in the analysis.

LH-PCR and T-RFLP proved to be highly reproducible methods, although the estimated peak size often deviated by 1–2 base pairs from the size predicted from the respective sequence. Despite these discrepancies, the methods were reproducible, with variances of ±0.3 bp for fragments up to 350 bp.

Comparisons of *Bacteroides/Prevotella* and *Bifidobacterium* gene profiles among 14 humans and 16 cows suggested insignificant intraspecies variation, mostly manifested as differences in proportions rather than species present. Human feces were collected from coworkers and their families, so it is possible that these individuals share intestinal flora (Caugant et al., *J. Hygiene* 92:377–84, 1984; Mehta et al., *Diagnostic Microbiology of Infectious Disease* 34:19–25, 1999). However, sewage samples from Tillamook and Corvallis (cities separated by 100 miles and a mountain range) also showed nearly identical patterns, indicating that the host-specific patterns were widely distributed. This does not mean that the commensal bacterial communities are identical in individuals from geographically distinct populations. Instead, it demonstrates that the method does not reveal variability at the level of the individual, but does reveal variability between host species.

Previous analyses of human fecal flora using culture techniques did not show major differences in bacterial species composition even when populations with different diets were compared (Finegold et al., "Normal Indigenous Intestinal Flora," in Hentges, *Human Intestinal Microflora in Health and Disease*, New York, Academic Press, 1983), although relative frequencies varied among individuals (Holdeman et al., *Appl. Environ. Microbiol.* 31:359–75, 1976). Other studies, however, suggested major differences in community composition of *Bifidobacterium* and *Lactobacillus* in humans (McCartney et al., *Appl. Environ. Microbiol.* 62:4608–13, 1996; and Kimura et al., *Appl. Environ. Microbiol.* 63:3394–8, 1997). The data indicates low intraspecific variation within a bacterial population.

These discrepancies may be explained by the differences in the methods used. Culturing bacteria from samples discriminates to the species level or even the strain level. Methods based on sizes and compositions of gene fragments, such as LH-PCR and T-RFLP, may discriminate only to the phylogenetic group or gene cluster level. It is possible that individuals harbor different species or strains of bacteria within a particular gene cluster, which would not necessarily be detected using the methods presented.

EXAMPLE 8

GenBank Accession Numbers

The GenBank accession numbers are as follows: AF233400, AF233401, AF233402, AF233403, AF233404, AF233405, AF233406, AF233407, AF233408, AF233409, AF233410, AF233411, AF233412, and AF233413. These sequences were used to develop initial primers to identify genetic markers.

EXAMPLE 9

Primer Design

Figure 7:
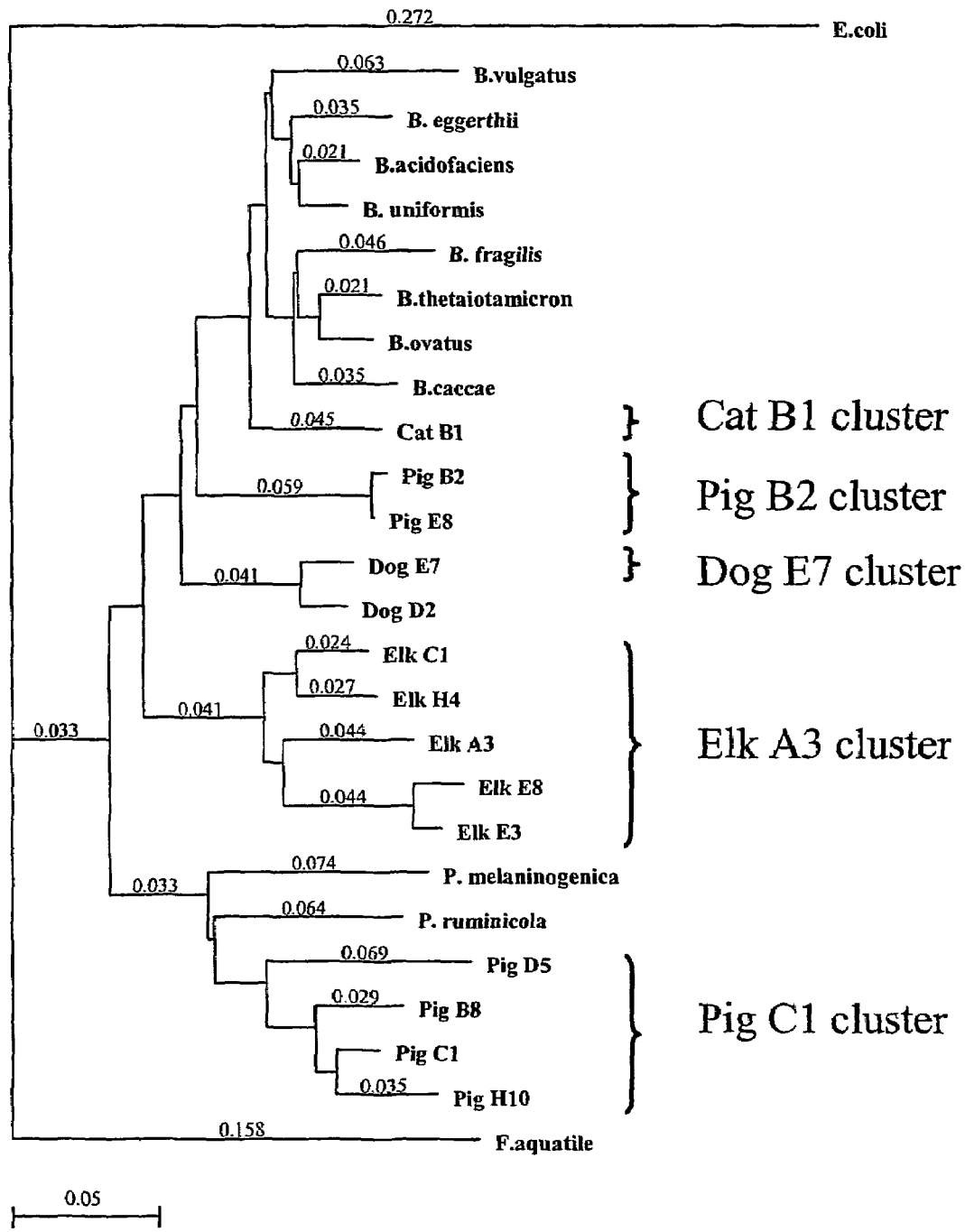
FIG. 7 shows a tree of phylogenetic relationships among partial 16S rDNA sequences (558 positions) cloned from fecal DNAs. Cat B1 cluster, Pig B2 cluster, Dog E7 cluster, Elk A3 cluster and Pig C1 cluster are *Bacteroides* bacterial sequences or sequence clusters that are unique to different host species: one group each from elk, dog, and cat, and two groups from pig. These host-specific bacterial sequences were used to design primers specific for each animal group. The tree was inferred by neighbor joining. Numbers above the branches are genetic distances, defined as the average number of sequence changes per position, and calculated by the Kimura-Nei algorithm.

The sequences of the additional clones combined with the sequence data already gathered allowed for the design of the primers shown in Table 3. Primers were designed by visual analysis or by using the Probe Design function of ARB (Strunk et al., *ARB, A Software Environment for Sequence Data*, Munich, Technische Universitat Munchen, 1996) and confirmed using CHECK_PROBE analysis of the Ribosomal Database Project (Maidak et al., *Nucleic Acids Res.* 22:3485–7, 1994) and Probe Match of ARB. Fecal DNAs from elk, pig, dog and cat were extracted and *Bacteroides* 16S rRNA genes were amplified. Species-specific sequence clusters of *Bacteroides-Prevotella* from elk, dog, cat, and pig (FIG. 7) were used to design host-species-specific primers for elk (CACAGCCGCTCGAAAG; SEQ ID NO: 9), dog (CCTTCCGTACACTCAGGG; SEQ ID NO: 10), Cat (ACCTGCCTTCCACTCG; SEQ ID NO: 11), and two primers for pig (TTCCCYTGTCCACGG; SEQ ID NO:12 and ATAGCCCAGCGAAAGTTG; SEQ ID NO: 13). The Dog E7 cluster, used to design the Dog132F primer specific for domestic pet feces, also includes CatE5 and Cat F3 sequences. The Cat B1cluster, used to design the Cat131F primer specific for cat feces, also includes CatG1 and Cat C8 sequences. The ELkA3 cluster was used to design the ELk149F primer specific for elk feces. The Pig B2 cluster was used to design the Pig134F primer, and the PigB2 cluster was used to design the Pig150F primer, both specific for pig feces.

TABLE 3

Host-species-specific primers for detection of fecal anaerobic bacteria

| Primer* | Sequence (5'-3') | | Target/Anneal. Temp. (° C.) |
|---|---|---|---|
| Bac708R | CAATCGGAGTTCTTCGTG | (SEQ ID NO: 3) | Bacteroides-Prevotella |
| CF128F | CCAACYTTCCCGWTACTC | (SEQ ID NO: 6) | Ruminant-specific fecal 16S rDNAs/58° C. |
| CF193F | TATGAAAGCTCCGGCC | (SEQ ID NO: 7) | Ruminant-specific fecal 16S rDNAs/55° C. |
| HF183F | ATCATGAGTTCACATGTCCG | (SEQ ID NO: 8) | Human-specific fecal 16S rDNAs/59° C. |
| HF134F | GCCGTCTACTCTTGGCC | (SEQ ID NO: 14) | Human-specific fecal 16S rDNAs/59° C. |
| Elk149F | CACAGCCGCTCGAAAG | (SEQ ID NO: 9) | Elk-specific fecal 16S rDNAs |
| Dog132F | CCTTCCGTACACTCAGGG | (SEQ ID NO: 10) | dog- and cat-specific fecal 16S rDNAs |
| Cat131F | ACCTGCCTTCCACTCG | (SEQ ID NO: 11) | Cat-specific fecal 16S rDNAs |
| Pig134F | TTCCCYTGTCCACGG | (SEQ ID NO: 12) | Pig-specific fecal 16S rDNAs |
| Pig150F | ATAGCCCAGCGAAAGTTG | (SEQ ID NO: 13) | Pig-specific fecal 16S rDNAs |

*Bac = Bacteroides-Prevotella;
HF = human-specific;
CF = ruminant specific.
Numbers correspond to the position within the E. coli 16S rRNA gene.
All forward primers were paired with Bac708R (SEQ ID NO: 3).

Using PCR primers specific for each gene cluster, host-specificity was confirmed by testing fecal DNAs from human and cow feces and from sewage samples. Genes corresponding to the HF8 cluster were detected in 11 out of 13 human fecal samples, all of the sewage samples, and none of the cow fecal samples (Table 4). Using the HF10 primers, a PCR product was detected in less than half of the sewage and human fecal samples. The HF10 primers allowed for the detection of products in one cow fecal sample. HF8 genes were more widely distributed among the humans, and primers for HF10 were not as specific as desired, hence, HF8 genes were tested in subsequent analyses. Genes from the CF151 and CF123 clusters were detected in all cow samples, but in none of the human or sewage samples.

TABLE 4

Distributions of host-specific genetic markers in feces from the targeted hosts.*

| | | Human Markers | | Cow Markers | |
|---|---|---|---|---|---|
| Target | N | HF8 Cluster | HF10 Cluster | CF123 Cluster | CF151 Cluster |
| Human | 13 | 11 | 6 | 0 | 0 |
| Sewage | 3 | 3 | 1 | 0 | 0 |
| Cow | 19 | 0 | 1 | 19 | 19 |

*Numbers of positive PCR results (2 rounds of 25 cycles each) out of N samples tested are reported.

To further determine the host-specificity of these primers, fecal samples collected from other animals in Tillamook and Corvallis were tested (Table 5). HF8 sequences were not detected in any samples from non-human sources. CF123 and CF151 sequences, however, were detected in all other ruminants tested.

TABLE 5

Distribution of host-specific genetic markers in feces from non-target animals.

| | | Human Marker | Cow Markers | |
|---|---|---|---|---|
| Animal | N | HF8 Cluster | CF123 Cluster | CF151 Cluster |
| Cat | 3 | 0 | 0 | 0 |
| Deer* | 3 | 0 | 2 | 3 |
| Dog | 3 | 0 | 0 | 0 |
| Duck | 3 | 0 | 0 | 0 |
| Elk* | 3 | 0 | 3 | 3 |
| Goat* | 1 | 0 | 1 | 1 |
| Llama** | 1 | 0 | 1 | 1 |
| Pig | 3 | 0 | 0 | 0 |
| Seagull | 3 | 0 | 0 | 0 |
| Sheep* | 4 | 0 | 4 | 4 |

Numbers of positive PCR results (2 rounds of 25 cycles each) out of N samples tested are reported.
*ruminants;
**pseudo-ruminants.

Sensitivity of the PCR and detection of the fecal markers were tested using plasmid DNAs and serial dilutions of feces or sewage. PCR sensitivity was approximately $1 \times 10^{-12}$ g DNA ($10^5$ gene copies) for all three plasmid DNAs. Detection of Bacteroides-Prevotella DNA was 2–4 times greater than fecal coliform detection (Table 6). Detection of CF123 genes was as sensitive as detection of fecal coliforms. Fecal coliform detection, however, was one to two times more sensitive than detection of CF151 genes. The sensitivity assay using cow fecal dilutions was repeated with feces from different cows, and similar results were obtained (Table 6).

TABLE 6

Detection limits for *Bacteroides-Prevotella* 16S rDNA, host-specific genetic markers, and fecal coliforms.

| Source of DNA | *Bacteroides-Prevotella**  | HF8 Cluster | CF123 Cluster | CF151 Cluster | Fecal Coliforms |
|---|---|---|---|---|---|
| Cow feces A | $2.8 \times 10^{-9}$ | ND | $2.8 \times 10^{-7}$ | $2.8 \times 10^{-5}$ | $2.8 \times 10^{-7}$ |
| Cow feces B | $3.6 \times 10^{-10}$ | ND | $3.6 \times 10^{-6}$ | $3.6 \times 10^{-5}$ | $3.6 \times 10^{-6}$ |
| Sewage | $1.4 \times 10^{-10}$ | $1.4 \times 10^{-6}$ | ND | ND | $1.4 \times 10^{-7}$ |

Results are from dilution assays using either cow feces or raw sewage.
Cow feces A and B are combinations of feces from different cows (4 cows each). Numbers are reported as g dry feces/L.
ND = not determined.
*Using Bac32F and Bac708R as described above.

The seven additional unique clones isolated from natural waters corresponded to the human and cow fecal markers previously identified. Hence, host-specific genetic markers are useful for identifying non-point sources of fecal pollution in coastal waters. Six of the clones were close phylogenetic relatives of the clones recovered from feces. The seventh clone, however, was more distantly related and its phylogenetic placement was not strongly supported by bootstrap analysis (FIG. 6). All the evidence, except the phylogeny, indicates the inclusion of this clone in the CF123 cluster.

Initial analysis of the fecal markers suggested that they were human and cow-specific. However, after testing feces from other animals, it was determined that the cow-specific markers were actually ruminant-specific. This is not surprising because ruminants have distinctive gastrointestinal systems, and likely would share many ruminal microbial flora (Stahl et al., *Appl. Environ. Microbiol.* 54:1079–84, 1988; and Amann et al., *J. Bact.* 172:762–70, 1990). Therefore, a positive PCR result for genes belonging to the CF123 or CF151 cluster does not rule out wildlife sources, but land use evaluation of the area being tested could determine the likelihood of an agricultural or wildlife source.

EXAMPLE 10

Sensitivity Analysis

Serial dilutions of fresh cow feces or raw sewage were added to 1-L samples of filter-sterilized bay water. Final concentrations in the 1-L samples ranged from $2 \times 10^{-7}$ mg (wet weight)/L to 2.0 mg/L. Samples were filtered onto a 0.2 µm Supor™ filter and stored in lysis buffer at −80° C. as described above. The percent solids of the fecal samples was estimated by weighing replicate samples of wet feces and drying with heat until no more weight was lost. To estimate percent solids of raw sewage, the solids were collected by centrifugation, the supernatants were decanted, and the samples were dried overnight with heat. DNAs extracted from the filters were amplified using Bac32F (SEQ ID NO: 1) and Bac708R (SEQ ID NO: 3) as described above, and the PCR products were visualized in a 1% agarose gel. Products were digested as described above. Samples were analyzed by T-RFLP, using 25 fmoles of the most concentrated dilution (2.0 mg/L), and equivalent volumes from all other dilutions.

EXAMPLE 11

Testing of Environmental Samples

Using the general and host-specific primers for fecal bacterial rDNA, a variety of river and estuarine water samples (collected from Tillamook Bay, Oreg. and three of its tributaries) were tested for the presence of *Bacteroides/Prevotella* and *Bifidobacterium* DNA and also for the marker genes. Water samples were collected from Tillamook Bay, Oreg. and its five major tributaries from June 1998 to April 1999.

FIG. 8 shows the sampling sites in Tillamook Bay and its tributaries and locations of NPDES (National Pollution Discharge Elimination System) or CAFO (Confined Animal Feeding Operation) permitted sites. Fecal coliforms in these samples ranged from 0 to 120 CFU/100 mL (Table 7). *Bacteroides/Prevotella* DNA was detected in all eight samples tested, but *Bifidobacterium* DNA was detected in only two of these samples. Additionally, the product yield of *Bifidobacterium* amplicons detected in these water samples was considerably less than that obtained from the same samples using *Bacteroides* primers. All seven host-specific genetic markers were detected in at least one water sample (Table 7, FIG. 4). In subsequent experiments, sequence data were used to validate the identities of the *Bacteroides/Prevotella* markers from water samples. Sequences from *Bacteroides/Prevotella* markers were recovered that belonged to the HF8, CF123, and CF151 gene clusters.

TABLE 7

Fecal coliform measurements and presence/absence of *Bifidobacterium* and *Bacteroides/Prevotella* host-specific markers in water samples.

| | | | *Bifidobacterium* | | | *Bacteroides/Prevotella* | | | |
|---|---|---|---|---|---|---|---|---|---|
| | | Fecal | 142- | | | | | | |
| Date Collected | Sample Type | Coliforms (CFU/100 ml) | 152 bp | 313 bp | 453 bp | 119 bp | 222 bp | 276 bp | 227 bp |
| Dec. 12, 1997 | river | 2 | + | − | + | nd | nd | + | + |
| Dec. 12, 1997 | river | 6 | − | − | − | − | − | − | + |
| May 17, 1998 | river | 120 | − | − | − | nd | nd | − | + |

TABLE 7-continued

Fecal coliform measurements and presence/absence of *Bifidobacterium* and *Bacteroides/Prevotella* host-specific markers in water samples.

| Date Collected | Sample Type | Fecal Coliforms (CFU/100 ml) | Bifidobacterium 142-152 bp | 313 bp | 453 bp | Bacteroides/Prevotella 119 bp | 222 bp | 276 bp | 227 bp |
|---|---|---|---|---|---|---|---|---|---|
| Oct. 30, 1998 | river | 36 | + | + | − | + | − | − | + |
| Oct. 30, 1998 | river mouth | 112 | − | − | − | + | + | − | + |
| Oct. 30, 1998 | estuary | 35 | − | − | − | − | − | − | + |
| Oct. 30, 1998 | estuary | 57 | − | − | − | + | + | − | + |
| Oct. 30, 1998 | estuary mouth | 0 | − | − | − | − | − | + | − |

"+" indicates the peak size was detected in the LH-PCR or T-RFLP analysis;
"−" indicates no peak was detected of that size;
"nd" indicates no data.

The sensitivity of detecting host-specific DNA in water samples was tested by conducting assays using filter-sterilized bay water amended with fresh feces or raw sewage. Feces and sewage were used rather than cultured organisms because fecal organisms were the intended targets. The limit of detection of host-specific markers varied, with the 222-bp cow-specific marker being the least sensitive ($2.8 \times 10^{-5}$ g dry feces/L), followed by the 119-bp human-specific marker ($6.8 \times 10^{-7}$ g dry sewage/L) and with the 227-bp cow-specific marker being the most sensitive ($2.8 \times 10^{-8}$ g dry feces/L).

Species were identified by composition differences in the *Bacteroides/Prevotella* and *Bifidobacterium* populations between human and cow feces. These differences are useful for, inter alia, identifying fecal-pollution non-point sources in coastal waters. The human-specific genetic markers within the *Bacteroides/Prevotella* group were closely related, but not identical, to *Bacteroides* species commonly found in human intestines and feces, *B. uniformis* and *B. vulgatus* (Salyers, *J. Bact.* 154:287–93, 1984). The cow-specific genetic markers formed new gene clusters within the *Bacteroides/Prevotella* group, which is in the *Cytophaga-Flavobacter-Bacteroides* phylum, a physiologically diverse, but phylogenetically similar, group (aster et al., *System. Appl. Microbiol.* 6:34–42, 1985; Gherna et al., *System. Appl. Microbiol.* 15:513–21, 1992). Gene clusters are sets of gene sequences more closely related to each other than to any characterized species; they have been found in many diverse natural bacterial populations (e.g. Giovannoni et al., *Nature* 345:60–3, 1990; Hales et al., *Appl. Environ. Microbiol.* 62:668–75, 1996; Ohkuma et al., *Appl. Environ. Microbiol.* 62:461–8, 1996; and Field et al., *Appl. Environ. Microbiol.* 63:63–70, 1997)

The *Bacteroides/Prevotella* group were better indicators than *Bifidobacterium* in coastal waters; however refinement of the primers used in the *Bifidobacterium* samples may improve the results.

Host-specific markers within the *Bacteroides/Prevotella* group were detected in all water samples from Tillamook Bay and its tributaries and in all fecal samples. Additionally, no fecal markers were detected in water samples collected from the Sargasso Sea or Crater Lake, Oreg., neither of which would be expected to have human or cow fecal pollution. The assay disclosed herein is designed to identify the presence or absence of a particular source; therefore direct comparisons to fecal coliforms are inappropriate. The presence of fecal markers in samples with no detectable coliforms (Table 4) is likely the result of differences in sensitivity or viability of the coliforms. The sample with no detectable coliforms was from the mouth of the estuary, where salinity is highest and coliforms would likely be stressed or dead. Methods for resuscitating stressed organisms were not practiced, so it is unlikely that such organisms would have been detected. DNA, however, has been detected from several days to two weeks cell death if conditions are optimal (Kreader, *Appl. Environ. Microbiol.* 64:4103–5, 1998).

Results from the sensitivity assays are comparable to results of other studies that used PCR to detect single *Bacteroides* species in feces (Kreader, *Appl. Environ. Microbiol.* 62:1102–6, 1996; Wang et al., *Appl. Environ. Microbiol.* 62:1242–7, 1996; and Kreader, *Appl. Environ. Microbiol.* 64:4103–5, 1998). The 119-bp human-specific marker and the 227-bp cow-specific marker appear to be more sensitive, as assayed by T-RPLP using general *Bacteroides/Prevotella* PCR primers. By designing primers specific to these markers, the sensitivity may be increased. The 222-bp cow-specific marker, which represents the same sequences as the 276-bp marker, was the least sensitive by 3–4 orders of magnitude. Some samples were also found to test positive for one, but not the other (Table 4). Since the sensitivity for these markers is much lower, it is possible that the source contamination was at or near the limit of detection; therefore, inconsistent detection of these two markers in the same water sample is not surprising.

Thus, the *Bacteroides/Prevotella* group is a good indicator for source identification of fecal contamination in water samples. The data provided shows: 1) human-specific and 2) cow-specific gene clusters of fecal markers from *Bacteroides/Prevotella*. The data disclosed herein demonstrates that these markers can be recovered from natural fresh-water and saltwater samples. The marker genes also have been identified phylogenetically as members of the *Bacteroides/Prevotella* group, but representing uncharacterized species.

Using the species-specific PCR assay described above, additional tests for the presence of human- and ruminant-specific genetic markers in 55 water samples collected from Tillamook Bay and its tributaries on five different sampling dates were performed. At least one host-specific fecal marker was detected in 27 of the 55 water samples (Table 8). Sixteen samples were positive for the human-specific marker HF8. For the ruminant-specific markers, eleven were positive for CF123, and twenty were positive for CF151. CF123 was not detected in any bay samples; HF8 and CF151 were found in both bay and river samples.

TABLE 8

Detection of human- and ruminant-specific markers in water samples.

| Sampling Date | Site* | HF8 (human) | CF123 (ruminant) | CF151 (ruminant) |
|---|---|---|---|---|
| Jun. 24, 1998 | B1 | − | − | − |
| Jun. 24, 1998 | B4 | − | − | − |
| Jun. 24, 1998 | B5 | + | − | − |
| Jun. 24, 1998 | B9 | − | − | − |
| Oct. 17, 1998 | B1 | − | − | − |
| Oct. 17, 1998 | B2 | + | − | + |
| Oct. 17, 1998 | B3 | − | − | + |
| Oct. 17, 1998 | B4 | − | − | + |
| Oct. 17, 1998 | B5 | + | − | − |
| Oct. 17, 1998 | B7 | − | − | − |
| Oct. 17, 1998 | B8 | − | − | − |
| Oct. 17, 1998 | R5 | + | − | − |
| Oct. 17, 1998 | T4 | + | − | − |
| Oct. 17, 1998 | W4 | − | − | − |
| Nov. 29, 1998 | B1 | − | − | − |
| Nov. 29, 1998 | B3 | − | − | − |
| Nov. 29, 1998 | B4 | − | − | − |
| Nov. 29, 1998 | K1 | − | − | − |
| Nov. 29, 1998 | K2 | − | − | − |
| Nov. 29, 1998 | M1 | − | − | − |
| Nov. 29, 1998 | R1 | − | − | − |
| Nov. 29, 1998 | R5 | − | − | − |
| Nov. 29, 1998 | T4 | − | − | − |
| Nov. 29, 1998 | W1 | − | − | − |
| Nov. 29, 1998 | W4 | − | − | − |
| Feb. 27, 1999 | R1 | − | − | − |
| Feb. 27, 1999 | R3 | + | + | + |
| Feb. 27, 1999 | R4 | + | + | + |
| Feb. 27, 1999 | T2 | − | − | − |
| Feb. 27, 1999 | T3 | + | + | + |
| Feb. 27, 1999 | W1 | − | − | − |
| Feb. 27, 1999 | W2 | − | − | − |
| Feb. 27, 1999 | W3 | − | − | − |
| Apr. 2, 1999 | B1 | − | + | + |
| Apr. 2, 1999 | B2 | − | + | + |
| Apr. 2, 1999 | B3 | + | − | + |
| Apr. 2, 1999 | B4 | + | − | + |
| Apr. 2, 1999 | B5 | + | − | + |
| Apr. 2, 1999 | B6 | − | − | + |
| Apr. 2, 1999 | B7 | + | − | + |
| Apr. 2, 1999 | B8 | + | − | − |
| Apr. 2, 1999 | B9 | − | − | − |
| Apr. 2, 1999 | R1 | − | − | − |
| Apr. 2, 1999 | R3 | + | + | + |
| Apr. 2, 1999 | R4 | − | − | − |
| Apr. 2, 1999 | R5 | + | + | + |
| Apr. 2, 1999 | R6 | + | − | + |
| Apr. 2, 1999 | R7 | + | − | − |
| Apr. 2, 1999 | T1 | − | + | + |
| Apr. 2, 1999 | T2 | − | + | + |
| Apr. 2, 1999 | T3 | − | + | + |
| Apr. 2, 1999 | T4 | − | + | + |

TABLE 8-continued

Detection of human- and ruminant-specific markers in water samples.

| Sampling Date | Site* | HF8 (human) | CF123 (ruminant) | CF151 (ruminant) |
|---|---|---|---|---|
| Apr. 2, 1999 | W1 | − | − | − |
| Apr. 2, 1999 | W3 | − | − | − |
| Apr. 2, 1999 | W4 | + | − | − |

*B = bay sites, K = Kilchis River sites, M = Miami River sites, R = Trask River sites, T = Tillamook River sites.
"+" indicates a positive PCR result,
"−" indicates a negative PCR result.
Not all sites were sampled on all sampling dates.

There was no significant correlation between sites positive for a marker and the distance to the nearest permitted point source. Distances from sample sites to the nearest NPDES (National Pollution Discharge Elimination System) site ranged from 0.02 to 8.7, and 0.2 to 11.9 km to the nearest CAFO (Confined Animal Feeding Operation) site (Table 9). Fecal markers were not detected at sites furthest away from a permitted site, but the distance varied for each marker. HF8 was never detected in samples more than 4.3 km from the nearest NPDES permitted site. Of the 18 samples collected from sites downstream of the nearest NPDES site, only five were positive for HF8. CF123 never was detected in samples more than 2.7 km from the nearest CAFO permitted site, and was found in only three of the samples downstream of the nearest CAFO site. CF151 was not detected in any samples over 5.9 km from the nearest CAFO site, and was found in five of the samples collected downstream of the nearest CAFO site.

TABLE 9

Distances (km) from each sampling site to the nearest permitted pollution source.

| Sampling Site | Nearest NPDES Permit* | Nearest CAFO permit# |
|---|---|---|
| B1 | (3.9) | (2.3) |
| B2 | 4.3 | (2.7) |
| B3 | 3.3 | (2.8) |
| B4 | 2.5 | (3.1) |
| B5 | (1.3) | (3.6) |
| B6 | (1.8) | (4.0) |
| B7 | 1.5 | (5.9) |
| B8 | 0.6 | (6.7) |
| B9 | (1.2) | (8.2) |
| K1 | 8.7 | 5.1 |
| K2 | (1.9) | 0.9 |
| M1 | 7.5 | 11.9 |
| R1 | 2.8 | 0.8 |
| R2 | 0.2 | (0.4) |
| R3 | (0.2) | (0.5) |
| R4 | (2.0) | (0.9) |
| R5 | 1.2 | (0.6) |
| R6 | 1.0 | (1.9) |
| T1 | 1.6 | (0.2) |
| T2 | 4.8 | (0.6) |
| T3 | 2.1 | 0.7 |
| T4 | 2.0 | (1.8) |
| W1 | 8.6 | 1.9 |
| W2 | 3.1 | (0.4) |
| W3 | 0.7 | 0.8 |
| W4 | (4.1) | (2.1) |

*NPDES = National Pollution Discharge Elimination System;
CAFO = Confined Animal Feeding Operation.
Numbers in parentheses indicate that the permitted sites are upstream from the sampling site.

Overall, the sites that were most frequently positive for human or ruminant markers were located in the bay, and on the Tillamook and Trask Rivers. No markers were detected in any samples from the Kilchis or Miami Rivers, and only one sample on the Wilson River (W4 on Apr. 2, 1999) tested positive for the HF8 marker. No sites on the Wilson River were positive for either of the ruminant-specific markers. Of all the sites in the bay and on the Tillamook and Trask Rivers, only two, R1 and B9, did not test positive for any of the markers on any sampling date.

Precipitation during sampling varied from 0 to almost 3 inches on the day of sampling (Table 10). Total precipitation during the five days prior to the sampling date ranged from 0.8 to over 10 inches. Rainfall was heaviest during the February sampling.

TABLE 10

Precipitation on sampling dates and five days prior to the sampling date.

| Sampling Date | Precipitation[#] | |
|---|---|---|
| | Day of sampling | Five Days Prior* |
| Jun. 24, 1998 | 0.77 | 0.8 |
| Oct. 17, 1998 | 0.19 | 2.19 |
| Nov. 29, 1998 | 0.77 | 7.43 |
| Feb. 27, 1999 | 2.87 | 10.59 |
| Apr. 2, 1999 | 0.0 | 2.14 |

[#]Precipitation data (in inches) was obtained from the Oregon Climate Service website and was measured at station Tillamook 1 W, 45' 27" W and 123' 52" N.
*Includes the day of sampling and the five days prior to sampling.

A sensitive and specific PCR diagnostic test was successfully applied to identify human- and ruminant-specific fecal contamination in river and estuarine water samples. The results indicate that the PCR assay is a rapid method for identifying non-point source pollution in coastal waters.

Fecal markers were detected in at least one sample on all sampling dates, except during November. Precipitation on the sampling date during November and the five days prior was quite high, averaging more than an inch per day. Heavier rains earlier in the week may have washed significant portions of fecal bacteria from the fields, thus leaving low numbers on the day of sampling. Additionally, the large amount of rain may have created a dilution effect, so that the concentrations of the markers were below the detection limits.

The same pattern was not observed in February, however, when rains were even higher. This may be attributed to the intensity of the storm. The rain on the day of sampling in February was much greater than in November (2.87 versus 0.77 inches, respectively), and the winds were quite high. The weather was severe enough to prevent sampling in the bay. The samples collected that day were sediment-laden and even the DNA extracts were brown, indicating high concentrations of contaminating substances. Other studies have documented increased fecal bacterial concentrations during storm events, due to resuspended sediments and increased survival of bacteria associated with sediments (Sherer et al., *J. Environ. Qual.* 21:591–5, 1992; Davies et al., *Appl. Environ. Microbiol.* 61:1888–96, 1995; and Baudart et al., *J. Environ. Qual.* 29:241–50, 2000).

The relationship between bacterial loads and rainfall, however, is not simple, and is affected by a complex set of interacting factors (see Baxter-Potter et al., *J. Environ. Qual.* 17:27–34, 1988, for a review). In addition to the intensity and amount of rainfall, other factors include slope of the land, sunlight, temperature, vegetation cover, soil properties, distance from the source to the sampling location, presence of toxic substances, and manure-management practices. The age of the manure deposits may also be a significant factor. Kress and Gifford (*Water Resources Bulletin* 20:61–7, 1984) studied the effect of varying intensities of rainfall on standard cowpies and found that the effect of rain intensity was related to dryness (or age) of the cowpie. They also found that release of fecal bacteria from 100-day old deposits was minimal compared to fresher fecal material.

A weak relationship was observed between the distance from the nearest permitted fecal pollution source (NPDES and CAFO permits) to the sampling site and presence of the markers, but again the relationship was not simple. Samples collected furthest from the permitted sites were always negative for the fecal markers, but the distances varied for the three markers. The sites that tested positive for the human-specific marker, HF8, could be attributed to sewage outfalls or sewage treatment plant effluents, but septic systems may also be contributing in some cases. There are over 1700 on-site sewage systems in the Tillamook Basin, with the majority concentrated on the Tillamook, the Trask, and the Wilson Rivers (Newell, "Water Quality: Measuring Health and Progress," in Human et al., *Tillamook Bay Environmental Characterization: A Scientific and Technical Summary*, Tillamook Bay National Estuary Project, Final Report, Garibaldi, Oreg., 1998). Surveys of these on-site sewage systems between 1988 and 1996 revealed a failure rate of 6 to 7% (Id.). Because samples were collected on a high tide, sampling sites located upstream of the source might be expected to be impacted more heavily than sites located downstream of the source. With a few exceptions, this pattern was observed for all three markers.

One of the ruminant markers, CF123, was found only in freshwater locations and river mouths, where salinity was less than 1 ppt. The sensitivity of detection of this marker under laboratory conditions (Table 7) was greater than the sensitivity of detection of the other ruminant marker, CF151. Salinity effects, however, were not investigated. CF151 was detected in nine samples that were negative for CF123. Most of these samples were located in the bay, which is affected by saline ocean waters. Samples were collected during high tides when the influence of saltwater would be greatest. It is possible that the species or strains that comprise CF123 die off more rapidly upon exposure to saline waters, as has been observed with other fecal bacteria (Sinton et al., *Appl. Environ. Microbiol.* 60:2040–2048, 1994; and Mezrioui et al., *Water Res.* 29:459–65, 1995). Studies of the effect of salinity on freshwater bacteria have shown that many riverine bacteria do not survive even in oligohaline conditions (Valdes et al., *Marine Biol.* 64:231–41, 1981; Bordalo, *J. Appl. Bacteriol.* 75:393–8, 1993; and Painchaud et al., *Appl. Environ. Microbiol.* 61:205–8, 1995). Although it is possible that not all fecal pollution from ruminants carry both markers, the data described above shows that both markers were found in all ruminant fecal samples tested.

CF123 and CF151 are useful for detecting ruminant-specific fecal pollution, so it is possible that deer and elk feces might have contributed to the signal. However, prevailing land-use patterns suggest that these sources would be insignificant in most cases. Most of the sampling sites were located in rural areas with a high density of agricultural operations. Additional evidence for the lack of wildlife contribution is that in sites upriver, such as R1 and W1, where wildlife would be most concentrated, no fecal markers ever were detected. Others have found that, in pristine areas, the contribution of wildlife, such as deer and elk, may contribute to fecal pollution in waterways, but the amount is insignificant compared to fecal pollution in agricultural areas (Niemi et al., *J. Environ. Qual.* 20:620–7, 1991).

EXAMPLE 12

Variant Primer/Probe Sequences

Disclosed herein are nucleotide sequences of several probes and primers. Distinctive functional characteristics of the disclosed probes and primers include, but are not limited to, their ability to be used to detect fecal contamination. This activity can readily be determined using the assays disclosed herein. In some embodiments, an additional distinctive characteristic is the ability of the disclosed probes and primers to be used to identify the host source of the contamination.

Having presented nucleotide sequences of probes and primers, this disclosure facilitates the creation of DNA molecules derived from those disclosed but which vary in their precise nucleotide sequence from those disclosed. Such variants can be obtained through standard molecular biology laboratory techniques and the sequence information disclosed herein.

Probe and primer variants, fragments, extensions, and polymorphisms will retain the ability to be used to detect fecal contamination.

In one embodiment, probe and primer variants retain at least 70%, 80%, 85%, 90%, 92%, 95%, 98%, 99%, or greater sequence identity to the primer sequences disclosed herein, and in particular embodiments at least this much identity to SEQ ID NOS: 1, 3, and 5–13. Variant and fragment sequences maintain the functional activity of the probes and primers as defined herein. Such activity can be readily determined using the assays disclosed herein.

Variant DNA molecules include those created by standard DNA mutagenesis techniques, for example, M13 primer mutagenesis. Details of these techniques are provided in Sambrook et al. (In: *Molecular Cloning: A Laboratory Manual*, Cold Spring Harbor, N.Y., 1989, Ch. 15). By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still possessing the functional characteristics of the disclosed probes and primers, are comprehended by this disclosure.

Probes and primers derived from those disclosed can also be defined as sequences which hybridize under stringent conditions to the sequences disclosed, or fragments thereof.

Hybridization conditions resulting in particular degrees of stringency vary depending upon the nature of the hybridization method and the composition and length of the hybridizing DNA used. Generally, the temperature of hybridization and the ionic strength (especially the Nat concentration) of the hybridization buffer determines hybridization stringency. Calculations regarding hybridization conditions required for attaining particular amounts of stringency are discussed by Sambrook et al. (*Molecular Cloning: A Laboratory Manual*, Cold Spring Harbor, N.Y., 1989, Chapters 9 and 11), herein incorporated by reference. By way of illustration, a hybridization experiment can be performed by hybridization of a DNA molecule (for example, a variant of a nucleic acid sequence shown in SEQ ID NOS: 1, 3, and 5–13) to a target DNA molecule (for example, a nucleic acid sequence shown in SEQ ID NOS: 1, 3, and 5–13) which has been electrophoresed in an agarose gel and transferred to a nitrocellulose membrane by Southern blotting (Southern, *J. Mol. Biol.* 98:503, 1975), a technique well known in the art.

Specific hybridization refers to the binding, duplexing, or hybridizing of a molecule only or substantially only to a particular nucleotide sequence when that sequence is present in a complex mixture (e.g. total cellular DNA or RNA). Specific hybridization may also occur under conditions of varying stringency.

Hybridization with a target probe labeled with $[^{32}P]$-dCTP is generally carried out in a solution of high ionic strength such as 6×SSC at a temperature that is about 5–25° C. below the melting temperature, $T_m$. For Southern hybridization experiments where the target DNA molecule on the blot contains 10 ng of DNA or more, hybridization is typically carried out for 6–8 hours using 1–2 ng/ml radiolabeled probe (specific activity equal to $10^9$ CPM/μg or greater). Following hybridization, the nitrocellulose filter is washed to remove background hybridization. Washing conditions should be as stringent as possible to remove background hybridization but retain a specific hybridization signal.

The term $T_m$ is the temperature (under defined ionic strength and pH) at which 50% of the target sequence remains hybridized to a perfectly matched probe or complementary strand. The $T_m$ of such a hybrid molecule may be estimated from the following equation (Bolton and McCarthy, *Proc. Natl. Acad. Sci. USA* 48:1390, 1962): $T_m=81.5°$ C.$-16.6(\log_{10}[Na^+])+0.41(\%$ G+C$)-0.63(\%$ formamide$)-(600/1)$; where 1=the length of the hybrid in base pairs.

This equation is valid for concentrations of $Na^+$ in the range of 0.01 M to 0.4 M, and it is less accurate for calculations of $T_m$ in solutions of higher $[Na^+]$. The equation is also primarily valid for DNAs whose G+C content is in the range of 30% to 75%, and it applies to hybrids greater than 100 nucleotides in length (the behavior of oligonucleotide probes is described in Sambrook et al. (*Molecular Cloning: A Laboratory Manual*, Cold Spring Harbor, N.Y., 1989, Ch. 11).

Thus, by way of example, for a 150 base pair DNA probe derived from the open reading frame of an Edaradd-isoform A cDNA (with a hypothetical % GC=45%), a calculation of hybridization conditions required to give particular stringencies may be made as follows. Assuming the filter is washed in 0.3×SSC solution following hybridization; $[Na^+]=0.045$ M; % GC=45%; [formamide]=0; l=150 base pairs; $T_m=81.5-16.6(\log_{10}[Na^+])+(0.41\times45)-(600/150)$; so $T_m=74.4°$ C.

The $T_m$ of double-stranded DNA decreases by 1–1.5° C. with every 1% decrease in homology (Bonner et al., *J. Mol. Biol.* 81:123, 1973). Therefore, for this example, washing the filter in 0.3×SSC at 59.4–64.4° C. will produce a stringency of hybridization equivalent to 90%; that is, DNA molecules with more than 10% sequence variation relative to the target cDNA (for example a nucleic acid sequence shown in SEQ ID NOS: 1, 3, and 5–13) will not hybridize. Alternatively, washing the hybridized filter in 0.3×SSC at 65.4–68.4° C. yields a hybridization stringency of 94%; that is, DNA with more than 6% sequence variation relative to the target cDNA will not hybridize. The above example is given by way of theoretical illustration. One skilled in the art will appreciate that other hybridization techniques can be utilized and that variations in experimental conditions will necessitate alternative calculations for stringency.

Examples of stringent conditions are those under which DNA molecules with more than 25%, 15%, 10%, 6% or 2% sequence variation (also termed "mismatch") will not hybridize. Longer sequences hybridize specifically at higher temperatures. An example of stringent conditions is a salt concentration of at least about 0.01 to 1.0 M Na ion concentration (or other salts) at pH 7.0 to 8.3 and a temperature of at least about 30° C. for short probes (e.g. 10 to 50 nucleotides). Stringent conditions can also be achieved with the addition of destabilizing agents such as formamide. For example, conditions of 5×SSPE (750 mM NaCl, 50 mM Na phosphate, 5 mM EDTA, pH 7.4) at 25–30° C. are suitable for allele-specific probe hybridizations.

A perfectly matched probe or primer has a sequence perfectly complementary to a particular target sequence. The test probe or primer is typically perfectly complementary to a portion (subsequence) of the target sequence. The term "mismatch probe" refers to probes whose sequence is deliberately selected not to be perfectly complementary to a particular target sequence.

The degeneracy of the genetic code further widens the scope of the present disclosure as it enables major variations in the nucleotide sequence of a DNA molecule while maintaining the amino acid sequence of the encoded protein. Because of the degeneracy of the genetic code, four nucleotide codon triplets, GCT, GCG, GCC and GCA, code for Ala. Thus, a nucleotide sequence could be changed at the third position to any of these codons without affecting the amino acid composition of the encoded protein or the characteristics of the protein. Based upon the degeneracy of the genetic code, variant DNA molecules may be derived from the DNA molecules disclosed herein using standard DNA mutagenesis techniques as described above, or by synthesis of DNA sequences. DNA sequences which do not hybridize under stringent conditions to the probe and primer sequences disclosed by virtue of sequence variation based on the degeneracy of the genetic code are also comprehended by this disclosure.

Probes and primers and their analogs hybridize by hydrogen bonding, which includes Watson-Crick, Hoogsteen, or reversed Hoogsteen hydrogen bonding, between complementary bases. Generally, nucleic acid consists of nitrogenous bases that are either pyrimidines (cytosine (C), uracil (U), and thymine(T)) or purines (adenine (A) and guanine (G)). These nitrogenous bases form hydrogen bonds with the bonding of a pyrimidine to a purine, and the bonding of a pyrimidine to a purine is referred to as "base pairing." More specifically, A will bond to T or U, and G will bond to C. "Complementary" refers to base pairing that occurs between two distinct nucleic acid sequences or two distinct regions of the same nucleic acid sequence.

"Specifically hybridizable" and "specifically complementary" are terms that indicate a sufficient degree of complementarity, such that stable and specific binding occurs between the oligonucleotide (or its analog) and the DNA or RNA target The oligonucleotide or oligonucleotide analog need not be 100% complementary to its target sequence to be specifically hybridizable. An oligonucleotide or analog is specifically hybridizable when such binding of the oligonucleotide or analog to the target DNA or RNA molecule allows for the detection of a complementary strand. There is a sufficient degree of complementarity to avoid non-specific binding of the oligonucleotide or analog to non-target sequences under conditions in which specific binding is desired, for example during PCR reactions. Such binding is referred to as specific hybridization.

Another method of describing the degree of basepair formation between nucleic acid sequences is in percentage complementarity. Percentage complementarity refers to the degree to which bases in one nucleic acid strand base pair with the bases in a second nucleic acid strand. Complementarity is conveniently described by the percentage, i.e., the proportion, of nucleotides that form base pairs between two strands or within a specific region or domain of two strands. For example, if 10 nucleotides of a 15-nucleotide oligonucleotide form base pairs with a targeted region of a DNA molecule, then the oligonucleotide is said to have 66.67% complementarity to the region of DNA targeted.

Sufficient complementarity occurs when a sufficient number of base pairs exist between the oligonucleotide and the target sequence to achieve detectable binding. When expressed or measured by percentage of base pairs formed, the percentage complementarity that fulfills this goal can range from as little as about 50% complementarity to full (100%) complementary. In general, sufficient complementarity is about 50%, such as about 75% complementarity, such as about 90% or 95% complementarity, such as about 98% or 100% complementarity.

A thorough treatment of the qualitative and quantitative considerations involved in establishing binding conditions that allow one skilled in the art to design appropriate oligonucleotides for use under the desired conditions is provided by Beltz et al., *Methods Enzymol* 100:266–85, 1983, and by Sambrook et al. (eds.), *Molecular Cloning: A Laboratory Manual*, 2nd ed., vols. 1–3, Cold Spring Harbor Laboratory Press, Cold Spring Harbor, N.Y., 1989.

Variant oligonucleotides are oligonucleotides that have one more base substitutions compared to the sequences shown in SEQ ID NOS: (i.e., naturally occurring bases such as A, T, C, G, or U, or synthetic bases such as those described below), one or more base deletions, and/or one or more base insertions, so long as the variant oligonucleotide substantially retains the activity of the original oligonucleotide, or has sufficient complementarity to a target sequence. For instance, a variant of the oligonucleotide shown in SEQ ID NO: 1 substantially would retain the activity of SEQ ID NO: 1, such that it would be useful for detecting the presence of fecal matter.

EXAMPLE 13

Stabilized Primers/Probes

To detect rDNA and/or rRNA, the probe or primer should be sufficiently stable to resist degradation during storage, and during temperature fluctuations, and to avoid degradation from potential contaminating nucleases caused by the repeated opening and closing of stock solutions containing the primer and/or the probe. Hence, it is often desirable to engineer the probes and/or primers to be nuclease-resistant and heat-stable so that they remain intact for extended periods of time. This can be done, for example, by substituting the normally occurring phosphodiester linkage, which connects the individual bases, with modified linkages. These modified linkages may, for example, be a phosphorothioate, methylphosphonate, phosphoditbioate, or phosphoselenate. Furthermore, a single probe or primer molecule may contain multiple substitutions in various combinations.

A probe or primer molecule also can be designed to contain different sugar molecules. For example, the molecule may contain the sugars ribose, deoxyribose or mixtures thereof, linked to a base. The bases give rise to the molecules' ability to bind complementarily to the target RNA and DNA. Additionally, as mentioned above, probes and primers need not be 100% complementary to the target RNA or DNA to detect the target.

The probes and/or primers can vary in length. Generally, a longer complementary region will give rise to a molecule with higher specificity. The probes and/or primers can be DNA or RNA, or chimeric mixtures or derivatives or modified versions thereof. The oligonucleotide can be modified at the base moiety, sugar moiety, or phosphate backbone.

In one embodiment, the probes and/or primers are single-stranded DNA (ssDNA) molecules, although the disclosure is not limited to such primers. An oligonucleotide can be modified at any position on its structure with substitutes generally known in the art. For example, a modified base moiety may be 5-fluorouracil, 5-bromouracil, 5-chlorouracil, 5-iodouracil, hypoxanthine, xanthine, acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N-6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl)uracil, and 2,6-diaminopurine.

In another embodiment, the polynucleotide includes at least one modified sugar moiety such as arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal, or analog thereof.

The relative ability of an oligomer such as a polynucleotide to bind to a complementary strand is compared by determining the melting temperature of a hybridization complex of a polypeptide and its complementary strand. Base stacking, which occurs during hybridization, is accompanied by a reduction in UV absorption (hypochromicity). A reduction in UV absorption indicates a higher $T_m$. The higher the $T_m$ the greater the strength of the binding of the hybridized strands. Generally, 100% complementarity between two nucleic acid sequences achieves optimal hybridization of a polynucleotide to its target RNA and/or DNA.

EXAMPLE 14

Non-Amplification-Based Detection Methods

Nucleic acid hybridization analysis generally involves the detection (using probes or primers) of very small numbers of specific target nucleic acids (DNA or RNA) among a large amount of non-target nucleic acids. In order to maintain high specificity, hybridization normally is carried out under the most stringent conditions, achieved through various combinations of temperature, salts, detergents, solvents, chaotropic agents, and denaturants.

Multiple-sample nucleic acid hybridization analysis has been conducted on a variety of filter and solid support formats (see Beltz et al., in Wu et al. (eds.), *Methods in Enzymology*, Vol. 100, Part B, Academic Press, New York, Chapter 19, pp. 266–308, 1985). One format, the so-called "dot blot" hybridization, involves non-covalent attachment of target DNAs to a filter. The dots are hybridized with a radioisotope-labeled probe(s). Dot blot hybridization gained wide-spread use, and many versions now have been developed (see Anderson et al., in Hames et al. (eds.), *Nucleic Acid Hybridization—A Practical Approach*, IRL Press, Washington D.C., Chapter 4, pp. 73–111, 1985). Dot blot hybridization has been developed farther for multiple analysis of genomic mutations (Nanibhushan and Rabin, in European Patent Application No. 0228075, filed Jul. 8, 1987) and for the detection of overlapping clones and the construction of genomic maps (Evans, U.S. Pat. No. 5,219,726, issued Jun. 15, 1993).

Sandwich hybridization, involves attaching oligonucleotide probes covalently to a solid support and using them to capture and detect multiple nucleic acid targets. (Ranki et al, *Gene* 21:77–85, 1983; Palva et al., UK Patent Application No. GB 2156074A, filed Oct. 2, 1985; Ranki et al., U.S. Pat. No. 4,563,419, issued Jan. 7, 1986; Malcolm et al., in published PCT Patent Application No. WO 86/03782, published Jul. 3, 1986; Stabinsky, U.S. Pat. No. 4,751,177, issued Jan. 14, 1988; Adams et al., in PCT Patent Application No. WO 90/01564, published Feb. 22, 1990; Wallace et al. *Nucleic Acids Research* 11:3543, 1979; and Connor et al., *Proc. Natl. Acad. Sci. USA* 80:278–82, 1983). Multiplex versions of these formats are called reverse dot blots.

A distinctive exception to the general difficulty in detecting low-copy-number target nucleic acids using a direct probe is the in-situ hybridization technique. This technique allows low-copy-number unique nucleic acid sequences to be detected in individual cells. In the in-situ format, target nucleic acid is naturally confined to the area of a cell or a nucleus at a relatively high local concentration. Furthermore, the probe/target hybridization signal is confined to a microscopic and morphologically distinct area; this makes it easier to distinguish a positive signal from artificial or non-specific signals than hybridization on a solid support.

In-situ hybridization, such a fluorescence in-situ hybridization (FISH), allows for the direct detection of nucleic acid sequences in a tissue section. A similar technique could be used to detect target nucleic acid sequences in a sample. A sample could be concentrated such that the bacteria were trapped on a filter or other support media. The concentrated immobilized bacteria could then be probed with a label probes.

Mimicking the in-situ hybridization in some aspects, new techniques are being developed for carrying out multiple sample nucleic acid hybridization analysis on micro-formatted multiplex or matrix devices (e.g., DNA chips) (see Barinaga, *Science*, 253:1489, 1991; and Bains, *Bio/Technology* 10:757–8, 1992). These methods usually attach specific DNA sequences to very small specific areas of a solid support, such as micro-wells of a DNA chip. These hybridization formats are micro-scale versions of the conventional reverse dot blot and sandwich hybridization systems.

Having illustrated and described methods for detecting fecal contamination using host-specific probes, it should be apparent to one skilled in the art that the disclosure can be modified in arrangement and detail without departing from such principles. In view of the many possible embodiments to which the principles of our disclosure may be applied, it should be recognized that the illustrated embodiments are only particular examples of the disclosure and should not be taken as a limitation on the scope of the disclosure. Rather, the scope of the disclosure is in accord with the following claims. We therefore claim as our invention all that comes within the scope and spirit of these claims.

We claim:

1. A method for detecting fecal contamination in a sample, comprising:
    contacting the sample with at least one nucleic acid molecule molecule consisting of at least 92% sequence identity to the nucleic acid sequence shown in SEQ ID NO: 1, 3, 5, 6, 7, 8, 9, 10, 11, 12, 13, or 14 and capable of binding to a nucleic acid sequence in a sample for detecting fecal contamination; and
    detecting binding of the nucleic acid molecule to the nucleic acid sequence in the sample, wherein a presence of binding is indicative of a presence of fecal contamination in the sample.

2. The method of claim 1, wherein the nucleic acid molecule capable of binding to the nucleic acid sequence in the sample for detecting fecal contamination is the nucleic acid sequence shown in SEQ ID NO: 1, 3, 5, 6, 7, 8, 9, 10, 11, 12, 13, or 14.

3. The method of claim 1, wherein the nucleic acid molecule capable of binding to the nucleic acid sequence in the sample for detecting fecal contamination is in a stabilized form and capable of binding to the nucleic acid sequence in the sample for detecting fecal contamination in the sample.

4. The method of claim 2, wherein the nucleic acid sequence shown in SEQ ID NO: 1, 3, 5, 6, 7, 8, 9, 10, 11, 12, 13, or 14 is in a stabilized form and capable of binding to the nucleic acid sequence in the sample for detecting fecal contamination in the sample.

5. The method of claim 1, wherein the nucleic acid molecule capable of binding to the nucleic acid sequence in the sample for detecting fecal contamination is further capable of identifying a host-source of fecal contamination in the sample.

6. The method of claim 1, wherein the nucleic acid molecule capable of binding to the nucleic acid sequence in the sample for detecting fecal contamination comprises a detectable label.

7. The method of claim 6, wherein the detectable label is a fluorescent molecule, a chemiluminescent molecule, a coenzyme, an enzyme substrate or a radioactive group.

8. The method of claim 1, wherein the fecal contamination is a fecal bacteria.

9. The method of claim 8, wherein the fecal bacteria is a *Bifidobacterium* or a member of *Bacteroides-Prevotella*.

10. The method of claim 1, wherein the sample is an environmental sample.

11. The method of claim 10, wherein the environmental sample is a water sample, a sediment sample, or suspended particle sample.

12. The method of claim 10, wherein the environmental sample is a soil sample.

13. The method of claim 1, wherein binding is detected by an amplification reaction.

14. The method of claim 13, wherein the amplification reaction is polymerase chain reaction (PCR).

15. The method of claim 1, wherein binding is detected by a non-amplification reaction.

16. The method of claim 15, wherein the non-amplification reaction is in-situ hybridization.

17. A nucleic acid molecule consisting of at least 92% sequence identity to the nucleic acid sequence shown in SEQ ID NO: 3, 5, 6, 7, 8, 9, 10, 11, 12, 13, or 14, and capable of binding to the nucleic acid sequence in a sample for detecting fecal contamination.

18. The nucleic acid molecule of claim 17, wherein the nucleic acid molecule is the nucleic acid sequence shown in SEQ ID NO: 3, 5, 6, 7, 8, 9, 10, 11, 12, 13, or 14, and capable of binding to the nucleic acid sequence in a sample for detecting fecal contamination.

19. The nucleic acid molecule of claim 17, wherein the nucleic acid molecule is further capable of identifying a host source of fecal contamination in the sample.

20. The nucleic acid molecule of claim 17, wherein the nucleic acid molecule comprises a detectable label.

21. A kit comprising at least two of the nucleic acid molecule of claim 17.

22. The method of claim 1, wherein the nucleic acid molecule capable of binding to the nucleic acid sequence in the sample for detecting fecal contamination consists of at least 95% sequence identity to the nucleic acid sequence shown in SEQ ID NO: 1, 3, 5, 6, 7, 8, 9, 10, 11, 12, 13, or 14.

23. A nucleic acid molecule consisting of at least 95% sequence identity to the nucleic acid sequence shown in SEQ ID NO: 3, 5, 6, 7, 8, 9, 10, 11, 12, 13, or 14, and capable of binding to the nucleic acid sequence in the sample for detecting fecal contamination.

24. A nucleic acid molecule, wherein the nucleic acid molecule consists of the nucleic acid sequence shown in SEQ ID NO: 1, 3, 5, 6, 7, 8, 9, 10, 11, 12, 13, or 14.

25. A method for detecting fecal contamination in a sample, comprising:

contacting the sample with at least one nucleic acid molecule consisting of at least 92% sequence identity to the nucleic acid sequence shown in SEQ ID NO: 3, 5, 6, 7, 8, 9, 10, 11, 12, 13, or 14 and capable of binding to the nucleic acid sequence in the sample for detecting fecal contamination; and detecting binding of the nucleic acid molecule to a nucleic acid sequence in the sample, wherein a presence of binding is indicative of a presence of fecal contamination in the sample.

* * * * *

UNITED STATES PATENT AND TRADEMARK OFFICE
CERTIFICATE OF CORRECTION

PATENT NO. : 7,118,870 B2
APPLICATION NO. : 10/381904
DATED : October 10, 2006
INVENTOR(S) : Field et al.

It is certified that error appears in the above-identified patent and that said Letters Patent is hereby corrected as shown below:

Column 20, line 62, "ELkA3" should be --ElkA3--.

Column 20, line 63, "ELk149F" should be --Elk149F--.

Column 24, Table 7, line 59, the spacing of the column headings is not aligned properly. The column headings should be aligned as follows:

| | | | Bifidobacterium | | | Bacteroides/Prevotella | | | |
|---|---|---|---|---|---|---|---|---|---|
| -- Date Collected | Sample Type | Fecal Coliforms (CFU/100ml) | 142-152 bp | 313 bp | 453 bp | 119 bp | 222 bp | 276 bp | 227 bp -- |

Column 25, line 47, "aster" should be --Paster--.

Column 30, line 32, "Human et al." should be --Hinzman et al.--.

Column 33, line 2, the extra spaces between "(60/150);" and "so" should be deleted so the text appears as follows: --(60/150); so--.

In the Claims:

Column 41, claim 1, "molecule molecule" should be --molecule--.

Signed and Sealed this

Twenty-ninth Day of May, 2007

JON W. DUDAS
*Director of the United States Patent and Trademark Office*

SEQUENCE LISTING

```
<160> NUMBER OF SEQ ID NOS: 14

<210> SEQ ID NO 1
<211> LENGTH: 18
<212> TYPE: DNA
<213> ORGANISM: Artificial Sequence
<220> FEATURE:
<223> OTHER INFORMATION: Primer/Probe

<400> SEQUENCE: 1
aacgctagct acaggctt                                                 18

<210> SEQ ID NO 2
<211> LENGTH: 18
<212> TYPE: DNA
<213> ORGANISM: Artificial Sequence
<220> FEATURE:
<223> OTHER INFORMATION: Primer/Probe

<400> SEQUENCE: 2
ccaatgtggg ggaccttc                                                 18

<210> SEQ ID NO 3
<211> LENGTH: 18
<212> TYPE: DNA
<213> ORGANISM: Artificial Sequence
<220> FEATURE:
<223> OTHER INFORMATION: Primer/Probe

<400> SEQUENCE: 3
caatcggagt tcttcgtg                                                 18

<210> SEQ ID NO 4
<211> LENGTH: 18
<212> TYPE: DNA
<213> ORGANISM: Artificial Sequence
```

```
<220> FEATURE:
<223> OTHER INFORMATION: Primer/Probe

<400> SEQUENCE: 4
gggtggtaat gccggatg                                                        18

<210> SEQ ID NO 5
<211> LENGTH: 21
<212> TYPE: DNA
<213> ORGANISM: Artificial Sequence
<220> FEATURE:
<223> OTHER INFORMATION: Primer/Probe

<400> SEQUENCE: 5
taagcgatgg actttcacac c                                                    21

<210> SEQ ID NO 6
<211> LENGTH: 18
<212> TYPE: DNA
<213> ORGANISM: Artificial Sequence
<220> FEATURE:
<223> OTHER INFORMATION: Primer/Probe
<220> FEATURE:
<221> NAME/KEY: misc_feature
<222> LOCATION: (6)..(6)
<223> OTHER INFORMATION: y = t/u or c
<220> FEATURE:
<221> NAME/KEY: misc_feature
<222> LOCATION: (13)..(13)
<223> OTHER INFORMATION: w = a or t/u

<400> SEQUENCE: 6
ccaacyttcc cgwtactc                                                        18

<210> SEQ ID NO 7
<211> LENGTH: 16
<212> TYPE: DNA
<213> ORGANISM: Artificial Sequence
<220> FEATURE:
<223> OTHER INFORMATION: Primer/Probe

<400> SEQUENCE: 7
tatgaaagct ccggcc                                                          16

<210> SEQ ID NO 8
<211> LENGTH: 20
<212> TYPE: DNA
<213> ORGANISM: Artificial Sequence
<220> FEATURE:
<223> OTHER INFORMATION: Primer/Probe

<400> SEQUENCE: 8
atcatgagtt cacatgtccg                                                      20

<210> SEQ ID NO 9
<211> LENGTH: 16
<212> TYPE: DNA
<213> ORGANISM: Artificial Sequence
<220> FEATURE:
<223> OTHER INFORMATION: Primer/Probe

<400> SEQUENCE: 9
cacagccgct cgaaag                                                          16

<210> SEQ ID NO 10
<211> LENGTH: 18
<212> TYPE: DNA
```

```
<213> ORGANISM: Artificial Sequence
<220> FEATURE:
<223> OTHER INFORMATION: Primer/Probe

<400> SEQUENCE: 10
ccttccgtac actcaggg                                                18

<210> SEQ ID NO 11
<211> LENGTH: 16
<212> TYPE: DNA
<213> ORGANISM: Artificial Sequence
<220> FEATURE:
<223> OTHER INFORMATION: Primer/Probe

<400> SEQUENCE: 11
acctgccttc cactcg                                                  16

<210> SEQ ID NO 12
<211> LENGTH: 15
<212> TYPE: DNA
<213> ORGANISM: Artificial Sequence
<220> FEATURE:
<223> OTHER INFORMATION: Primer/Probe
<220> FEATURE:
<221> NAME/KEY: misc_feature
<222> LOCATION: (6)..(6)
<223> OTHER INFORMATION: y = t/u or c

<400> SEQUENCE: 12
ttcccytgtc cacgg                                                   15

<210> SEQ ID NO 13
<211> LENGTH: 18
<212> TYPE: DNA
<213> ORGANISM: Artificial Sequence
<220> FEATURE:
<223> OTHER INFORMATION: Primer/Probe

<400> SEQUENCE: 13
atagcccagc gaaagttg                                                18

<210> SEQ ID NO 14
<211> LENGTH: 17
<212> TYPE: DNA
<213> ORGANISM: Artificial Sequence
<220> FEATURE:
<223> OTHER INFORMATION: Primer/Probe

<400> SEQUENCE: 14
gccgtctact cttggcc                                                 17
```